United States Patent [19]

Chan

[11] Patent Number: 5,169,835
[45] Date of Patent: Dec. 8, 1992

[54] PREGANCY SPECIFIC PROTEINS APPLICATIONS

[75] Inventor: Wai-Yee Chan, Gaithersburg, Md.

[73] Assignee: Oklahoma Medical Research Foundation, Oklahoma City, Okla.

[21] Appl. No.: 390,409

[22] Filed: Aug. 7, 1989

Related U.S. Application Data

[63] Continuation-in-part of Ser. No. 298,638, Jan. 18, 1989.

[51] Int. Cl.[5] .................... A61K 35/50; A61K 37/02; C07K 15/14
[52] U.S. Cl. .......................................... 514/8; 514/12; 514/21; 435/240.2; 435/244; 530/395; 530/397; 424/583
[58] Field of Search ............... 435/240.2, 244; 514/12, 514/21, 8; 530/395, 397; 424/583

[56] References Cited

U.S. PATENT DOCUMENTS 4,818,709  4/1989  Primus ............................. 435/7.23

FOREIGN PATENT DOCUMENTS 59-214767  12/1984  Japan.

OTHER PUBLICATIONS

Chan, "The Pregnancy-Specific B1-Glycoprotein Family", (1991) Adv. Contr. Deliv. Sys., vol. VII, pp. 21–52.
Williams et al. (1990) Exp. Hematol 18: 69–72.
Patchen et al. (1991) Blood 77(3):472–480.
Ishibashi et al. (1989) Blood 74(4):1241–1244.
Asano et al. (1990) Blood 75(8):1602–1605.
Whicher et al. (1990) Clin. Chem 36/7:1269–1272.
C. H. W. Horne, et al., *Placental Proteins*, (Springer Verlag 1979) pp. 143–160.
Tatarinov and Masyukevich, Bull. Exp. Biol. Med. 69, 666–668 (1970).
Y. S. Tatarinov, *Placental Proteins*, (Springer Verlag 1979) 161–171.
Lin, et al., *J. Clin. Invest.* 54, 576–582 (1974).
Heikinheimo, et al., *J. Clin. Endocr. Metab.* 51, 1432–1436 (1980).
Rosen, *Pregnancy Proteins* 223–234 (1982).
Bohn, *Blut* 24, 292–302 (1972) (Summary which is translated).
W. Jones, et al., *Pregnancy Proteins*, (Academic Press, New York 1982) pp. 241–250.
J. G. Grudzinskas, et al., *Pregnancy Proteins*, (Academic Press, New York 1982) pp. 251–259.

(List continued on next page.)

*Primary Examiner*—Christine M. Nucker
*Assistant Examiner*—Kay K. Kim
*Attorney, Agent, or Firm*—Kilpatrick & Cody

[57] ABSTRACT

At least seven genes have been identified which encode proteins generally identified as pregnancy specific protein (SP1), also known as pregnancy specific beta glycoprotein (PSBG). These genes have been found using human placental SP1 labelled cDNA in a number of mammalian species, including human, baboon, cow, sheep, goat, pig and rat, and non-mammalian species, including fish and bird. The genes are classified on the basis of their nucleotide sequence, structure, glycosylation sites, restriction enzyme mapping, and tissue of origin. Genes have been found in cells of human placenta origin (three groups); in intestinal cells; in cells of both testis and placental origin; in tissue of testis origin; and in HeLa cells. One clone encodes a SP1-like protein which is specifically found in placenta and appears to have a hydrophobic C-terminal region, indicating that it is membrane bound. These cDNAs are at least 65% homologous with some members of the immunoglobulin gene superfamily such as CEA. Methods for making and using the DNA sequences, proteins, and antibodies to the proteins are also described, particularly for diagnostic work. Immunosuppressive activity and growth promoting activities have also been demonstrated by suppression of lymphocyte proliferation and inducement of megakaryocytopoiesis, respectively.

3 Claims, 17 Drawing Sheets

OTHER PUBLICATIONS

J. G. Williams, *Genetic Engineering*, vol. 1 (Academic Press, New York 1981) at pp. 1–8.

A. G. Ahmed, et al., *British Journal of Obstetrics and Gynecology* 90: 604–611 (1983).

Chou, *Oncodevelop. Biol. Med.* 4, 319–326 (1983).

Bischof, *Contri. Gynecol. Obstet.* 12, 6–92 (1984).

P. Bischof, *Gynecology and Obstetrics*, 12: 6–12 (1984) with concluding remarks and references.

S. W. Rosen, et al., *Placenta* 7: 575–594 (1986).

L. Johnston-Dow, et al., *Bio-Techniques* 5(8): 754–765 (1987).

W. Y. Chan, et al., *Fed. Proc.* 44(5): 1461 (1985).

W. Y. Chan, et al., *Pediatric Research* 19(4): 152A (1985).

W. Y. Chan, et al., *J. Cell. Biol.* 105(4): 258a (1987).

W. Y. Chan, et al., *Am. J. Hum. Genet.* 41(3): A149 (1987).

W. Qiu, et al., Fed. Proc. 46(6): 2186 (1987).

L. Tease, et al., *Fed. Proc.* 45(6): 1512 (1986).

L. A. Tease, et al., FASEB J. 2(5): A1686 (1988).

W. Y. Chan, et al., FASEB J. 2(5): A1686 (1988).

W. Y. Chan, et al., *Am. J. Hum. Genet.* 43: 152–159 (1988).

W. Y. Chan, et al., *Human Reproduction* 3(5): 677–685; 687–692 (1988).

W. Y. Chan, et al., *DNA* 7(8): 545–555 (1988).

S. Watanabe, et al., J. Biol. Chem. 263(4): 2049–2054 (1988).

S. Watanabe, et al., *Biochemical and Biophysical Research Communications* 152: 762–768 (1988).

Streydio, et al., *Biochem. Biophys. Research Comm.*, 154(1), 130–137 (Jul. 1988).

Beauchemin et al. (1987) Mol. Cellular Biol 7: 3221–3230.

Rooney et al. (1988) Gene 71: 439–449.

```
  1 GACAGCCGTG CTCAGAGAGT TTCTGGATCC TAGGCTTATC TCCACAGAGG AGAACACACA   60

61 AGCAGCAGAGACCATGGGAACCCTCTCAGCCCCTCCCTGCACACAGCGCATCAAATGGAA  120
                 M  G  T  L  S  A  P  P  C  T  Q  R  I  K  W  K

121 GGGGCTCCTGCTCACAGCATCACTTTTAAACTTCTGGAACCTGCCCACCACTGCCCAAGT  180
     G  L  L  L  T  A  S  L  L  N  F  W  N  L  P  T  T  A  Q  V

181 CACGATTGAAGCCGAGCCAACCAAAGTTTCCGAGGGGAAGGATGTTCTTCTACTTGTCCA  240
     T  I  E  A  E  P  T  K  V  S  E  G  K  D  V  L  L  L  V  H

241 CAATTTGCCCCAGAATCTTACCGGCTACATCTGGTACAAAGGGCAAATGAGGGACCTCTA  300
     N  L  P  Q  N  L  T  G  Y  I  W  Y  K  G  Q  M  R  D  L  Y

301 CCATTACATTACATCATATGTAGTAGACGGTGAAATAATTATATATGGGCCTGCATATAG  360
     H  Y  I  T  S  Y  V  V  D  G  E  I  I  I  Y  G  P  A  Y  S

361 TGGACGAGAAACAGCATATTCCAATGCATCCCTGCTGATCCAGAATGTCACCCGGGAGGA  420
     G  R  E  T  A  Y  S  N  A  S  L  L  I  Q  N  V  T  R  E  D

421 CGCAGGATCCTACACCTTACACATCATAAAGGGAGATGATGGGACTAGAGGAGTAACTGG  480
     A  G  S  Y  T  L  H  I  I  K  G  D  D  G  T  R  G  V  T  G

481 ACGTTTCACCTTCACCTTACACCTGGAGACTCCTAAGCCCTCCATCTCCAGCAGCAACTT  540
     R  F  T  F  T  L  H  L  E  T  P  K  P  S  I  S  S  S  N  L

541 AAATCCCAGGGAGACCATGGAGGCTGTGAGCTTAACCTGTGACCCTGAGACTCCAGACGC  600
     N  P  R  E  T  M  E  A  V  S  L  T  C  D  P  E  T  P  D  A

601 AAGCTACCTGTGGTGGATGAATGGTCAGAGCCTCCCTATGACTCACAGCTTGAAGCTGTC  660
     S  Y  L  W  W  M  N  G  Q  S  L  P  M  T  H  S  L  K  L  S

661 CGAAACCAACAGGACCCTCTTTCTATTGGGTGTCACAAAGTATACTGCAGGACCCTATGA  720
     E  T  N  R  T  L  F  L  L  G  V  T  K  Y  T  A  G  P  Y  E

721 ATGTGAAATACGGAACCCAGTGAGTGCCAGCCGCAGTGACCCAGTCACCCTGAATCTCCT  780
     C  E  I  R  N  P  V  S  A  S  R  S  D  P  V  T  L  N  L  L

781 CCCGAAGCTGCCCAAGCCCTACATCACCATCAACAACTTAAACCCCAGGGAGAATAAGGA  840
     P  K  L  P  K  P  Y  I  T  I  N  N  L  N  P  R  E  N  K  D

841 TGTCTTAAACTTCACCTGTGAACCTAAGAGTGAGAACTACACCTACATTTGGTGGCTAAA  900
     V  L  N  F  T  C  E  P  K  S  E  N  Y  T  Y  I  W  W  L  N

901 TGGTCAGAGCCTCCCGGTCAGTCCCAGGGTAAAGCGACCCATTGAAAACAGGATCCTCAT  960
     G  Q  S  L  P  V  S  P  R  V  K  R  P  I  E  N  R  I  L  I

961 TCTACCCAGTGTCACGAGAAATGAAACAGGACCCTATCAATGTGAAATACGGGACCGATA 1020
     L  P  S  V  T  R  N  E  T  G  P  Y  Q  C  E  I  R  D  R  Y

1021 TGGTGGCATCCGCAGTGACCCAGTCACCCTGAATGTCCTCTATGGTCCAGACCTCCCCAG 1080
     G  G  I  R  S  D  P  V  T  L  N  V  L  Y  G  P  D  L  P  R

1081 AATTTACCCTTCATTCACCTATTACCGTTCAGGAGAAGTCCTCTACTTGTCCTGTTCTGC 1140
     I  Y  P  S  F  T  Y  Y  R  S  G  E  V  L  Y  L  S  C  S  A

1141 GGACTCTAACCCACCGGCACAGTATTCTTGGACAATTAATGAAAAGTTTCAGCTACCAGG 1200
     D  S  N  P  P  A  Q  Y  S  W  T  I  N  E  K  F  Q  L  P  G

1201 ACAAAAGCTCTTTATCCGCCATATTACTACAAAGCATAGCGGGCTCTATGTTTGCTCTGT 1260
     Q  K  L  F  I  R  H  I  T  T  K  H  S  G  L  Y  V  C  S  V

1261 TCGTAACTCAGCCACTGGCAAGGAAAGCTCCAAATCCATGACAGTCGAAGTCTCTGACTG 1320
     R  N  S  A  T  G  K  E  S  S  K  S  M  T  V  E  V  S  D  W
```

FIGURE 2

```
1321  GACAGTTCCCTGAATTCTACTAGTACCTCCAATTCCATTTTCTCCCATGGAATCACTAAG  1380
         T   V   P   *

1381  AGCAAGACCCACTCTGTTCCAGAAGCCCTATAAGCTGGAGGTGGACAACTCAATGTAAAT  1440

1441  TTCATGGGAAAACCCTTGTACGTGAAGCATGAGCCACTCAGAACTCACCAAAATATTCGA  1500

1501  CACCATAACAACAGATGCTCAAACTGTAAACCAGGACAACAAGTGGATGACTTCACACTG  1560

1561  TGGACAGTTTTTCCCAAGATGTCAGAACAAGACTCCCCATCATGATGAGGCTCTCCCCCC  1620

1621  TCTTAACTGTCCTTGCTCATGCCTGCCTCTTTCACTTGGCAGGATAATGCAGTCATTAGA  1680

1681  ATTTCACATGTAGTAGCTTCTGAGAGTAACAACAGAGTGTCAGATATGTCATCTCAACCT  1740

1741  CAAACTTTTACATAACATCTCAGGGGGAAATGTGGCTCTCTCCACCTTGCATACAGGGCT  1800

1801  CCCAATAGAAATGAACACAGAGATATTGCCTGTGTGTTTGCAGAGAAGATGGTTTGTATG  1860

1861  AAGACGTAGGAAAGCTGAAATTATAATAGAGTCCCCTTTAAATCCACATTGTGTGGATGG  1920

1921  CTCTTGCCTTTCCTAAGAGATACATTGAACCCGAATTC  1958
```

FIGURE 2 CONTINUED

```
  1 GCAGGAGCACTTCTACTTGTCCACAATTTGCCCCAGAATCTTCCTGGCTACTTCTGGTAC   60
  1 A  G  A  L  L  L  V  H  N  L  P  Q  N  L  P  G  Y  F  W  Y    20

61 AAAGGGGAAATGACGGACCTCTACCATTACATTATATCGTATATAGTTGATGGAAAAATA  120
 21 K  G  E  M  T  D  L  Y  H  Y  I  I  S  Y  I  V  D  G  K  I    40

121 ATTATATATGGGCCTGCATACAGTGGAAGAGAAACAGTATATTCCAACGCATCCTGCTG   180
 41 I  I  Y  G  P  A  Y  S  G  R  E  T  V  Y  S  N  A  S  L  L    60

181 ATCCAGAATGTCACCCGGAAGGATGCAGGAACCTACACCTTACACATCATAAAGCGAGGT  240
 61 I  Q  N  V  T  R  K  D  A  G  T  Y  T  L  H  I  I  K  R  G    80
                                         N     Rn
241 GATGAGACTAGAGAAGAAATTCGACATTTCACCTTCACCTTATACTTGGAGACTCCCAAG  300
 81 D  E  T  R  E  E  I  R  H  F  T  F  T  L  Y  L  E  T  P  K   100

301 CCCTACATCTCCAGCAGCAACTTAAACCCCAGGGAGGCCATGGAGGCTGTGCGCTTAATC  360
101 P  Y  I  S  S  S  N  L  N  P  R  E  A  M  E  A  V  R  L  I   120

361 TGTGATCCTGAGACTCTGGACGCAAGCTACCTATGGTGGATGAATGGTCAGAGCCTCCCT  420
121 C  D  P  E  T  L  D  A  S  Y  L  W  W  M  N  G  Q  S  L  P   140

421 GTGACTCACAGGTTGCAGCTGTCCAAAACCAACAGGACCCTCTATCTATTTGGTGTCACA  480
141 V  T  H  R  L  Q  L  S  K  T  N  R  T  L  Y  L  F  G  V  T   160

481 AAGTATATTGCAGGACCCTATGAATGTGAAATACGGAACCCAGTGAGTGCCATTCGCAGT  540
161 K  Y  I  A  G  P  Y  E  C  E  I  R  N  P  V  S  A  I  R  S   180
                                Rn     Rc
541 GACCCAGTCACCCTGAATCTCCTCCATGGTCCAGACCTCCCCAGAATTTACCCTTCATTC  600
181 D  P  V  T  L  N  L  L  H  G  P  D  L  P  R  I  Y  P  S  F   200

601 ACCTATTACCGTTCAGGAGAAAACCTCGACTTGTCCTGCTTCACGGAATCTAACCCACCG  660
201 T  Y  Y  R  S  G  E  N  L  D  L  S  C  F  T  E  S  N  P  P   220

661 GCAGAGTATTTTTGGACAATTAATGGGAAGTTTCAGCAATCAGGACAAAAGCTCTTTATC  720
221 A  E  Y  F  W  T  I  N  G  K  F  Q  Q  S  G  Q  K  L  F  I   240

721 CCCCAAATTACTAGAAATCATAGCGGGCTCTATGCTTGCTCTGTTCATAACTCAGCCACT  780
241 P  Q  I  T  R  N  H  S  G  L  Y  A  C  S  V  H  N  S  A  T   260
                                                    Rc     C
781 GGCAAGGAAATCTCCAAATCCATGACAGTCAAAGTCTCTGGTAAGTGGATCCCAGCATCC  840
261 G  K  E  I  S  K  S  M  T  V  K  V  S  G  K  W  I  P  A  S   280

841 TTGGCAGTAGGGTTTTATGTGGAGTCTATCTGGCTTTCAGAGAAGAGTCAGGAAAACATT  900
281 L  A  V  G  F  Y  V  E  S  I  W  L  S  E  K  S  Q  E  N  I   300

901 TTTATTCCCAGCCTGTGTCCCATGGGCACAAGCAAATCCCAAATTCTCCTCCTGAACCCT  960
301 F  I  P  S  L  C  P  M  G  T  S  K  S  Q  I  L  L  L  N  P   320

961 CCCAATTTGTCTCTACAGACTCTCTTCTCCTTGTTTTCTGTTTTCTTATGGCTGACCTT  1020
321 P  N  L  S  L  Q  T  L  F  S  L  F  F  C  F  L  M  A  D  L   340

1021 GTGTCTGGCCTGAAAAAGGTAGGGAGGGGCTTTATCAGCCCTGAGCCCTATGTGGTAGA  1080
341 V  S  G  L  K  K  V  G  R  G  L  Y  Q  P  *                  360

1081 AGAGGCTTCAGAGAGGGACAAGAAGGGAATTCCAAGGCAGCGTCCGCAGGTCGTGGTCAC  1140

1141 CTGCCAGCGACTGTCTCAGACTGGGCAGGGAGGCTTTGGCATGACTTAAGAGGAAGGGCA  1200

1201 GTCTTGGGCCCGCTATGCAGGTCCTGGCAAACCTGGCTGCCCTGTCTCCATCCCTGTCCC  1260

1261 TCAGGGTAGCACCATGGCAGGACTGGGGGAACTGGAGTGTCCTTGCTGTATCCCTGTTGT  1320

1321 GAGGTTCCTTCCAGGGGCTGGCACTGAAGCAAGGGTGCTGGGACCCCATGGCCTTCAGCC  1380

1381 CTGGCTGAGCAACTGGGCTGTAGGGCAGGGCACTTCTGAGGTCAGGTCTTGGTAGGTGCC  1440
```

FIGURE 3

```
1441  TGCATCTGTCTGCCTTCTGGCTGACAATCCTGGAAATCTGTTCTCCAGAATCAGGCCAAA   1500
1501  AAGTTCACAGTCAAATGGGGAGGGGTATTCTTCATGCAGGAGACCCCTAGGCCCTGGAGG   1560
1561  CTGCAACATACCTCAATCCTGTCCCAGGCCGGATCCTCCTGAAGCCCTTTTCGCAGCACT   1620
1621  GCTATCCTCCAAAGCCATTGTAAATGTGTGTACAGTGTGTATAAACCTTCTTCTTCTTTT   1680
1681  TTTTTTTTAAACTGAGGATTGTCATTAAACACAGTTGTTTTCTAAAAAAAAAAAAAAAA   1740
1741  AAAAAAAAAAAAA   1753
```

FIGURE 3 CONTINUED

```
   1  CCTAGGCTCATCTCCACAGGGGAGAACACACAGACAGCAGAGACCATGGGACCCCTCTCA    60
                                                      M  G  P  L  S

61  GCCCCTCCCTGCACTCAGCACATCACCTGGAAGGGGCTCCTGCTCACAGCATCACTTTTA   120
      A  P  P  C  T  Q  H  I  T  W  K  G  L  L  L  T  A  S  L  L

121  AACTTCTGGAACCTGCCCACCACTGCCCAAGTAATAATTGAAGCCAAGCCACCCAAAGTT   180
      N  F  W  N  L  P  T  T  A  Q  V  I  I  E  A  K  P  P  K  V

181  TCCGAGGGGAAGGATGTTCTTCTACTTGTCCACAATTTGCCCCAGAATCTTACTGGCTAC   240
      S  E  G  K  D  V  L  L  L  V  H  N  L  P  Q  N  L  T  G  Y

241  ATCTGGTACAAAGGGCAAATGACGGACCTCTACCATTACATTACATCATATGTAGTAGAC   300
      I  W  Y  K  G  Q  M  T  D  L  Y  H  Y  I  T  S  Y  V  V  D

301  GGTCAAATTATATATGGGCCTGCCTACAGTGGACGAGAAACAGTATATTCCAATGCATCC   360
      G  Q  I  I  Y  G  P  A  Y  S  G  R  E  T  V  Y  S  N  A  S

361  CTGCTGATCCAGAATGTCACACAGGAGGATGCAGGATCCTACACCTTACACATCATAAAG   420
      L  L  I  Q  N  V  T  Q  E  D  A  G  S  Y  T  L  H  I  I  K
                                                     N←—→R1n
 421  CGAGGCGATGGGACTGGAGGAGTAACTGGATATTTCACTGTCACCTTATACTCGGAGACT   480
      R  G  D  G  T  G  G  V  T  G  Y  F  T  V  T  L  Y  S  E  T

481  CCCAAGCCCTCCATCTCCAGCAGCAACTTAAACCCCAGGGAGGTCATGGAGCTGTGCGC   540
      P  K  P  S  I  S  S  S  N  L  N  P  R  E  V  M  E  A  V  R

▽
 541  TTAATCTGTGATCCTGAGACTCCGGATGCAAGCTACCTGTGGTTGCTGAATGGTCAGAAC   600
      L  I  C  D  P  E  T  P  D  A  S  Y  L  W  L  L  N  G  Q  N

601  CTCCCTATGACTCACAGGTTGCAGCTGTCCAAAACCAACAGGACCCTCTATCTATTTGGT   660
      L  P  M  T  H  R  L  Q  L  S  K  T  N  R  T  L  Y  L  F  G

▼
 661  GTCACAAAGTATATTGCAGGACCCTATGAATGTGAAATACGGAACCCAGTGAGTGCCAGC   720
      V  T  K  Y  I  A  G  P  Y  E  C  E  I  R  N  P  V  S  A  S
                                        R1n←—→R2n
 721  CGCAGTGACCCAGTCACCCTGAATCTCCTCCCGAAGCTGCCCATGCCTTACATCACCATC   780
      R  S  D  P  V  T  L  N  L  L  P  K  L  P  M  P  Y  I  T  I

▼
 781  AACAACTTAAACCCCAGGGAGAAGAAGGATGTGTTAGCCTTCACCTGTGAACCTAAGAGT   840
      N  N  L  N  P  R  E  K  K  D  V  L  A  F  T  C  E  P  K  S

841  CGGAACTACACCTACATTTGGTGGCTAAATGGTCAGAGCCTCCCGGTCAGTCCGAGGGTA   900
      R  N  Y  T  Y  I  W  W  L  N  G  Q  S  L  P  V  S  P  R  V

901  AAGCGACCCATTGAAAACAGGATACTCATTCTACCCAGTGTCACGAGAAATGAAACAGGA   960
      K  R  P  I  E  N  R  I  L  I  L  P  S  V  T  R  N  E  T  G

▼
 961  CCCTATCAATGTGAAATACGGGACCGATATGGTGGCATCCGCAGTAACCCAGTCACCCTG  1020
      P  Y  Q  C  E  I  R  D  R  Y  G  G  I  R  S  N  P  V  T  L
       R2n←—→R2c
1021  AATGTCCTCTATGGTCCAGACCTCCCCAGAATTTACCCTTCATTCACCTATTACCGTTCA  1080
      N  V  L  Y  G  P  D  L  P  R  I  Y  P  S  F  T  Y  Y  R  S

▼
1081  GGAGAAAACCTCGACTTGTCCTGCTTTGCGGACTCTAACCCACCGGCAGAGTATTTTGG  1140
      G  E  N  L  D  L  S  C  F  A  D  S  N  P  P  A  E  Y  F  W

1141  ACAATTAATGGGAAGTTTCAGCTATCAGGACAAAAGCTCTTTATCCCCCAAATTACTACA  1200
      T  I  N  G  K  F  Q  L  S  G  Q  K  L  F  I  P  Q  I  T  T

▼
1201  AATCATAGCGGGCTCTATGCTTGCTCTGTTCGTAACTCAGCCACTGGCAAGGAAATCTCC  1260
      N  H  S  G  L  Y  A  C  S  V  R  N  S  A  T  G  K  E  I  S
                         .R2c←—→C
1261  AAATCCATGATAGTCAAAGTCTCTGGTCCCTGCCATGGAAACCAGACAGAGTCTCATTAA  1320
      K  S  M  I  V  K  V  S  G  P  C  H  G  N  Q  T  E  S  H  *
```

FIGURE 4

```
1321  TGGCTGCCACAATAGAGACACTGAGAAAAAGAACAGGTTGATACCTTCATGAAATTCAAG  1380
1381  ACAAAGAAGAAAAAAACTCAATGTTATTGGACTAAATAATCAAAAGGATAATGTTTTCAT  1440
1441  AATTTTTTATTGGAAAATGTGCTGATTCTTGGAATGTTTTATTCTCCAGATTTATGAACT  1500
1501  TTTTTCTTCAGCAATTGGTAAAGTATACTTTTGTAAACAAAAATTGAAACATTTGCTTT   1560
1561  TGCTCTCCCGCCC  1573
```

FIGURE 4 CONTINUED

```
  1  CATATAGTGGACGAGAAACAGCATATTCCAATGCATCCCTGCTGATCCAGAATGTCACCC   60
  1    TyrSerGlyArgGluThrAlaTyrSerAsnAlaSerLeuLeuIleGlnAsnValThrA   20

61  GGGAGGACGCAGGATCCTACACCTTACACATCATAAAGGGAGATGATGGGACTAGAGGAG  120
 21    rgGluAspAlaGlySerTyrThrLeuHisIleIleLysGlyAspAspGlyThrArgGlyV   40

121  TAACTGGACGTTTCACCTTCACCTTACACCTGGAGACTCCTAAGCCCTCCATCTCCAGCA  180
 41    alThrGlyArgPheThrPheThrLeuHisLeuGluThrProLysProSerIleSerSerS   60

181  GCAACTTAAATCCCAGGGAGACCATGGAGGCTGTGAGCTTAACCTGTGACCCTGAGACTC  240
 61    erAsnLeuAsnProArgGluThrMetGluAlaValSerLeuThrCysAspProGluThrP   80

241  CAGACGCAAGCTACCTGTGGTGGATGAATGGTCAGAGCCTCCCTATGACTCACAGCTTGA  300
 81    roAspAlaSerTyrLeuTrpTrpMetAsnGlyGlnSerLeuProMetThrHisSerLeuL  100

301  AGCTGTCCGAAACCAACAGGACCCTCTTTCTATTGGGTGTCACAAAGTATACTGCAGGAC  360
101    ysLeuSerGluThrAsnArgThrLeuPheLeuLeuGlyValThrLysTyrThrAlaGlyP  120

361  CCTATGAATGTGAAATACGGAACCCAGTGAGTGCCAGCCGCAGTGACCCAGTCACCCTGA  420
121    roTyrGluCysGluIleArgAsnProValSerAlaSerArgSerAspProValThrLeuA  140

421  ATCTCCTCCCGAAGC  435
141    snLeuLeuProLys  145
```

FIGURE 5

```
   1  GAATTCTACTAGTTCCTCCAATTCCATTTTCTTCCATGGAATCGCTAAGAAAAAGACCCA    60
      |||||||||||||| ||||||||||||||||| |||||||||| ||||||  |||||||
1332  GAATTCTACTAGTACCTCCAATTCCATTTTCTCCCATGGAATCACTAAGAGCAAGACCCA  1391

61  CTCTGTTCCAGAAGCCCTATAAGCTGGAGGTGGACAACTCAATGTAAATTTCATGGGAAA   120
      ||||||||||||||||||||||||||||||||||||||||||||||||||||||||||||
1392  CTCTGTTCCAGAAGCCCTATAAGCTGGAGGTGGACAACTCAATGTAAATTTCATGGGAAA  1451

121  ACCCTTGTACCTGAAGCGTGAGCCACTCAGAACTCACTAAAATGTTCGACACCATAACAA   180
      |||||||||| ||||| ||||||||||||||||||| ||||| |||||||||||||||||
1452  ACCCTTGTACGTGAAGCATGAGCCACTCAGAACTCACCAAAATATTCGACACCATAACAA  1511

181  CAGATGCTCAAACTGTAAACCAGGACAACAAGTGGATGACTTCACACTGTGGACAGTTTT   240
      ||||||||||||||||||||||||||||||||||||||||||||||||||||||||||||
1512  CAGATGCTCAAACTGTAAACCAGGACAACAAGTGGATGACTTCACACTGTGGACAGTTTT  1571

241  TCCCAAGATGTCAGAACAAGACTCCCCATCATGATGAGGCTCTCACCCCTCTTAACTGTC   300
      |||||||||||||||||||||||||||||||||||||||||||||  |||||||||||||
1572  TCCCAAGATGTCAGAACAAGACTCCCCATCATGATGAGGCTCTCCCCCCTCTTAACTGTC  1631

301  CTTGCTCATGCCTGCCTCTTTCACTTGGCAGGATAATGCAGTCATTAGAATTTCACATGT   360
      ||||||||||||||||||||||||||||||||||||||||||||||||||||||||||||
1632  CTTGCTCATGCCTGCCTCTTTCACTTGGCAGGATAATGCAGTCATTAGAATTTCACATGT  1691

361  AGTAGCTTCTGAGGGTAACAATAGAGTGTCAGATATGTCATCTCAACC.CAAACTTTTAC   420
      ||||||||||||| |||||||||||||||||||||||||||||||||| |||||||||||
1692  AGTAGCTTCTGAGAGTAACAACAGAGTGTCAGATATGTCATCTCAACCTCAAACTTTTAC  1751

421  ATAACATCTCAGGGGGAAATGTGGCTCTCTCCACCTTGCATACAGGACTCCCAATAGAAA   480
      |||||||||||||||||||||||||||||||||||||||||||||||| |||||||||||
1752  ATAACATCTCAGGGGGAAATGTGGCTCTCTCCACCTTGCATACAGGGCTCCCAATAGAAA  1811

481  TGAACACAGAGATATTGCCCGTGTGTTTGCAGATAAGATGGTTTCTATGAAGAGGTAGGA   540
      ||||||||||||||||||| |||||||||||||| |||||||||| ||||||| ||||||
1812  TGAACACAGAGATATTGCCTGTGTGTTTGCAGAGAAGATGGTTTGTATGAAGACGTAGGA  1871

541  AAGCTGAAATTATAATAGAGTCCCCTTTAAATGCACATTCTGTGGATGGCTCTCGCCATT   600
      ||||||||||||||||||||||||||||||||  |||||| ||||||||||||| ||  |
1872  AAGCTGAAATTATAATAGAGTCCCCTTTAAATCCACATTGTGTGGATGGCTCTTGCC.TT  1931

601  TCCTAAGAGATACATTG    617
      |||||||||||||||||
1932  TCCTAAGAGATACATTG   1948
```

FIGURE 6

```
                                            IVS1◄─┐
  1  GGGGGGCCGTGCGGACCTGGGGAAGAGGATTCCAAACAGAAAAATGCCAAGCATCACTTT    60
                                                │ A  S  L  L

61  TAAACTTCTGGAACCCGCCTACCACTGCCCAAGTCACGATTGAAGCCGAGCCAACCAAAG   120
      N  F  W  N  P  P  T  T  A  Q  V  T  I  E  A  E  P  T  K  V

121  TTTCCAAGGGGAAGGACGTTCTTCTACTTGTCCACAATTTGCCCCAGAATCTTGCTGGCT   180
      S  K  G  K  D  V  L  L  L  V  H  N  L  P  Q  N  L  A  G  Y

181  ACATCTGGTACAAAGGGCAAATGAAGGACCTCTACCATTACATTACATCATACGTAGTAG   240
      I  W  Y  K  G  Q  M  K  D  L  Y  H  Y  I  T  S  Y  V  V  D

241  ATGGTCAAATAATTATATATGGGCCTGCATACAGTGGACGAGAAACAGTATATTCCAATG   300
      G  Q  I  I  I  Y  G  P  A  Y  S  G  R  E  T  V  Y  S  N  A
                                                            ─  ─
301  CATCCCTGCTGATCCAGAATGTCACCCGGGAGGACGCAGGATCCTACACCTTACACATCG   360
      S  L  L  I  Q  N  V  T  R  E  D  A  G  S  Y  T  L  H  I  V
      ─                                                   N◄─┬─►IVS2
361  TAAAGCGAGGTGATGGGACTAGAGGAGAAACTGGACATTTCACCTTCACCTTATACCGTC   420
      K  R  G  D  G  T  R  G  E  T  G  H  F  T  F  T  L  Y │

421  ATTCCTTGGACTCTGCTCTATCTTTAGAGGTCACTGGCTCAAGTCAGCCACTATGAGACA   480

481  CCTGGGAAAACTGCCCCACCTTGTGGCTCCACTGCCTGATGACTGAACTGACCTCCGGAC   540

541  TTGACTCTGTTCTCCCCTGTGTTATTTCTGCTGAAGTACCCAGTCCCAGGTCAGGCTTTC   600

601  CAGTATCCAAAGGGTTTAAAGACAATTGGAAGTTCCATCACCCATCTCTAGGATGTCCTT   660

661  GGCAAGGGAAGCTGCAGAGAAAACATACCTCGGGCGGCAAAGTAAGACTGAAACTAAGAA   720
                            . IVS2◄─┐
721  GATTCCAGCACTGCATGCTCCAAGTGAGGACCACAAGTGGAGACTCCCAAGCCCTCCATC   780
                                    │ E  T  P  K  P  S  I

781  TCCAGCAGCAACTTATACCCCAGGGAGGACATGGAGGCTGTGAGCTTAACCTGTGATCCT   840
      S  S  S  N  L  Y  P  R  E  D  M  E  A  V  S  L  T [C] D  P

841  GAGACTCCGGACGCAAGCTACCTGTGGTGGATGAATGGTCAGAGCCTCCCTATGACTCAC   900
      E  T  P  D  A  S  Y  L  W  W  M  N  G  Q  S  L  P  M  T  H

901  AGCTTGCAGTTGTCCAAAAACAAAAGGACCCTCTTTCTATTTGGTGTCACAAAGTACACT   960
      S  L  Q  L  S  K  N  K  R  T  L  F  L  F  G  V  T  K  Y  T

961  GCAGGACCCTATGAATGTGAAATACGGAACCCAGTGAGTGCCAGCCGCAGTGACCCAGTC  1020
      A  G  P  Y  E [C] E  I  R  N  P  V  S  A  S  R  S  D  P  V
          . R1n ◄─┬─► R2n
1021 ACCCTGAATCTCCTCCCGAAGCTGCCCAAGCCCTACATCACCATCAACAACTTAAACCCC  1080
      T  L  N  L  L │ P  K  L  P  K  P  Y  I  T  I  N  N  L  N  P

1081 AGGGAGAATAAGGATGTCTTAGCCTTCACCTGTGAACCTAAGAGTGAGAACTACACCTAC  1140
      R  E  N  K  D  V  L  A  F  T [C] E  P  K  S  E  N  Y  T  Y
                                                         ─  ─  ─
1141 ATTTGGTGGCTAAATGGTCAGAGCCTCCCGGTCAGTCCCAGGGTAAAGCGACCCATTGAA  1200
      I  W  W  L  N  G  Q  S  L  P  V  S  P  R  V  K  R  P  I  E

1201 AACAGGATCCTCATTCTACCCAGTGTCACGAGAAATGAAACAGGACCCTATCAATGTGAA  1260
      N  R  I  L  I  L  P  S  V  T  R  N  E  T  G  P  Y  Q [C] E
                                          ─  ─  ─        .R2n ◄─┬─► R2c
1261 ATACAGGACCGATATGGTGGCATCCGCAGTTACCCAGTCACCCTGAATGTCCTCATTAC   1320
      I  Q  D  R  Y  G  G  I  R  S  Y  P  V  T  L  N  V  L │ L  T
```

FIGURE 7

```
1321  TACAAAGCATAGCGGGCTCTATGCTTGCTCTGTTCGTAACTCAGCCACTGGCATGGAAAG  1380
       T   K   H   S   G   L   Y   A  [C]  S   V   R   N   S   A   T   G   M   E   S
                                    R2c ◄─┬─► C
1381  CTCCAAATCCATGACAGTCAAAGTCTCTGCTCCTTCAGGAACAGGACATCTTCCTGGCCT  1440
       S   K   S   M   T   V   K   V   S   A   P   S   G   T   G   H   L   P   G   L

1441  TAATCCATTATAGCAGCCGTGATGTCATTTCTGTATTTCAGGAAGACTGGCAGACAGTTG  1500
       N   P   L   *

1501  CTTTCATTCTTCCTCAAAGTATTTACCATCAGCTACAGTCCAAAATTGCTTTTGTTCAA   1560

1561  GGAGATTTATGAAAAGACTCTGACAAGGACTCTTGAATACAAGTTCCTGATAACTTCAAG  1620

1621  ATCATACCACTGGACTAAGAACTTTCAAAATTTTAATGAACAGGCTGATACTTCATGAAA  1680

1681  TTCAAGACAAAGAAAAAAACCCAATTTTATTGGACTAAATAGTCAAAACAATGTTTTCAT  1740

1741  AATTTTCTATTTGAAAATGTGCTGATTCTTTGAATGTTTTATTCTCCAGATTTATGCACT  1800

1801  TTTTTTCTTCAGCAATTGGTAAAGTATACTTTTGTAAACAAAAATTGAAACATTTGCTTT  1860

1861  TGCTCCCTAAGTGCCCCAGAATTGGGAAACTATTCAGGAGTATTCATATGTTTATGGTAA  1920

1921  TAAAGTTATCTGCACAAGTTCAAAAAAAAAAAAAAAA  1957
```

FIGURE 7 CONTINUED

```
  1 CCCTCTCAGCCCCTCCCTGCACACACCTCATCACCTGGAAGGGGCTCCTGCTCACAGCAT  60
    L  S  A  P  P  C  T  H  L  I  T  W  K  G  L  L  L  T  A  S

61 CACTTTTAAACTTCTGGAATCCGCCCACAACTGCCCAAGTCACGATTGAAGCCCAGCCAC 120
    L  L  N  F  W  N  P  P  T  T  A  Q  V  T  I  E  A  Q  P  P

121 CCAAAGTTTCTGAGGGGAAGGATGTTCTTCTACTTGTCCACAATTTGCCCCAGAATCTTG 180
    K  V  S  E  G  K  D  V  L  L  L  V  H  N  L  P  Q  N  L  A

181 CTGGCTACATTTGGTACAAAGGGCAAATGACATACCTCTACCATTACATTACATCATATG 240
    G  Y  I  W  Y  K  G  Q  M  T  Y  L  Y  H  Y  I  T  S  Y  V

241 TAGTAGACGGTCAAAGAATTATATATGGGCCTGCATACAGTGGAAGAGAAAGAGTATATT 300
    V  D  G  Q  R  I  I  Y  G  P  A  Y  S  G  R  E  R  V  Y  S

301 CCAATGCATCCCTGCTGATCCAGAATGTCACGCAGGAGGATGCAGGATCCTACACCTTAC 360
    N  A  S  L  L  I  Q  N  V  T  Q  E  D  A  G  S  Y  T  L  H

361 ACATCATAAAGCGACGCGATGGGACTGGAGGAGTAACTGCACATTTCACCTTCACCTTAC 420
    I  I  K  R  R  D  G  T  G  G  V  T  A  H  F  T  F  T  L  H
    N ←―→ R1n
421 ACCTGGAGACTCCCAAGCCCTCCATCTCCAGCAGCAACTTAAATCCCAGGGAGGCCATGG 480
    L  E  T  P  K  P  S  I  S  S  S  N  L  N  P  R  E  A  M  E

481 AGGCTGTGATCTTAACCTGTGATCCTGAGACTCCAGCCGCAAGCTACCAATGGTGGATGA 540
    A  V  I  L  T  C  D  P  E  T  P  A  A  S  Y  Q  W  W  M  N

541 ATGGTCAGAGCCTCCCTATGACTCACAGGTTGCAGCTGTCCAAAACCAACAGGACCCTCT 600
    G  Q  S  L  P  M  T  H  R  L  Q  L  S  K  T  N  R  T  L  F

601 TTATATTTGGTGTCACAAAGTATATTGCAGGACCCTATGAATGTGAAATACGGAACCCAG 660
    I  F  G  V  T  K  Y  I  A  G  P  Y  E  C  E  I  R  N  P  V
                                          R1n ←―→ R2n
661 TGAGTGCCAGCCGCAGTGACCCAGTCACCCTGAATCTCCTCCCAAAGCTGTCCAAGCCCT 720
    S  A  S  R  S  D  P  V  T  L  N  L  L  P  K  L  S  K  P  Y

721 ACATCACAATCAACAACTTAAACCCCAG 748
    I  T  I  N  N  L  N  P
```

FIGURE 8

```
  1  AGAGCATTCCTGGAGCTCAAGCGTCTCTACAAAGAGGTGGACAGAGAAGACAGCAGAGAC   60
 61  CATGGGACCCCCCTCAGCCCCTCCCTGCAGATTGCATTTCCCCTGGAAGGAGGTCCTGCT  120
      M  G  P  P  S  A  P  P  C  R  L  H  F  P  W  K  E  V  L  L
                                                        ▽
121  CACAGCCTCACTTCTAACCTTCTGGAACCCACCCACCACTGCCAAGCTCACTATTGAATC  180
      T  A  S  L  L  T  F  W  N  P  P  T  T  A  K  L  T  I  E  S
181  CACGCCGTTCAATGTCGCAGAGGGGAAGGAGGTTCTTCTACTCGCCCACAACCTGCCCCA  240
      T  P  F  N  V  A  E  G  K  E  V  L  L  A  H  N  L  P  Q
241  GAATCGTATTGGTTACAGCTGGTACAAAGGCGAAAGAGTGGATGGCAACAGTCTAATTGT  300
      N  R  I  G  Y  S  W  Y  K  G  E  R  V  D  G  N  S  L  I  V
301  AGGATATGTAATAGGAACTCAACAAGCTACCCCAGGGCCCGCATACAGTGGTCGAGAGAC  360
      G  Y  V  I  G  T  Q  Q  A  T  P  G  P  A  Y  S  G  R  E  T
361  AATATACCCCAATGCATCCCTGCTGATCCAGAACGTCACCCAGAATGACACAGGATTCTA  420
      I  Y  P  N  A  S  L  L  I  Q  N  V  T  Q  N  D  T  G  F  Y
                  ─         ─            ─         ─
421  TACCCTACAAGTCATAAAGTCAGATCTTGTGAATGAAGAAGCAACTGGACAGTTCCATGT  480
      T  L  Q  V  I  K  S  D  L  V  N  E  E  A  T  G  Q  F  H  V
      N ◄────► R1n
481  ATACCCGGAGCTGCCCAAGCCCTCCATCTCCAGCAACAACTCCAACCCTGTGGAGGACAA  540
      Y  P  E  L  P  K  P  S  I  S  S  N  N  S  N  P  V  E  D  K
                                          ─  ─  ─
541  GGATGCTGTGGCCTTCACCTGTGAACCTGAGACTCAGGACACAACCTACCTGTGGTGGAT  600
      D  A  V  A  F  T  C  E  P  E  T  Q  D  T  T  Y  L  W  W  I
601  AAACAATCAGAGCCTCCCGGTCAGTCCCAGGCTGCAGCTGTCCAATGGCAACAGGACCCT  660
      N  N  Q  S  L  P  V  S  P  R  L  Q  L  S  .  N  G  N  R  T  L
         ─  ─  ─                                          ─  ─  ─
661  CACTCTACTCAGTGTCACAAGGAATGACACAGGACCCTATGAGTGTGAAATACAGAACCC  720
      T  L  L  S  V  T  R  N  D  T  G  P  Y  E  C  E  I  Q  N  P
                        ─  ─  ─
                                      R1n ◄──► R1c
721  AGTGAGTGCGAACCGCAGTGACCCAGTCACCTTGAATGTCACCTATGGCCCGGACACCCC  780
      V  S  A  N  R  S  D  P  V  T  L  N  V  T  Y  G  P  D  T  P
              ─  ─  ─              ─  ─  ─
781  CACCATTTCCCCTTCAGACACCTATTACCGTCCAGGGGCAAACCTCAGCCTCTCCTGCTA  840
      T  I  S  P  S  D  T  Y  Y  R  P  G  A  N  L  S  L  S  C  Y
                                          ─  ─  ─
841  TGCAGCCTCTAACCCACCTGCACAGTACTCCTGGCTTATCAATGGAACATTCCAGCAAAG  900
      A  A  S  N  P  P  A  Q  Y  S  W  L  I  N  G  T  F  Q  Q  S
                                                ─  ─
901  CACACAAGAGCTCTTTATCCCTAACATCACTGTAATAATAGTGGATCCTATACCTGCCA  960
      T  Q  E  L  F  I  P  N  I  T  V  N  N  S  G  S  Y  T  C  H
                              ─  ─     ─  ─  ─
                                                    R1c ◄────►
961  CGCCAATAACTCAGTCACTGGCTGCAACAGGACCACAGTCAAGACGATCATAGTCACTGA 1020
      A  N  N  S  V  T  G  C  N  R  T  T  V  K  T  I  I  V  T  D
                                    ─  ─  ─
1021 TAAT 1024
      N
```

FIGURE 9

N-Terminal Domain

```
              1
SP1  N Con   MGXLSAPPCT QRIXWKGLLL TASLLNFWNL PTTAQVTIEA XPXKVSEGKD
     hCEA N  .SEP....HR WC.P.QR... .....T...P ....KL...S T.FN.A...E
     hNCA N  ...p.....R LHVP..EV.. .....T...P ....KL...S T.FN.A...E

51
SP1  N Con   VLLLVHNLPQ NLTGYIWYKG QMRDLYHYIT SYVVDGXIII YGPAYSGRET
     hCEA N  .......... H.F..S.... ERV.GNRQ.I G..IGT.QAT P........I
     hNCA N  ....A..... .R...S.... ERV.GNSL.V G..IGT.QAT P.........

101
SP1  N Con   AYSNASLLIQ NVTREDAGSY TLHIIKRXDG TRGVTGXFTF TLH
     hCEA N  I.P....... .IIQN.T.F. ...V..SDLV NEEA..Q.R  VY
     hNCA N  I.P....... ...QN.T.F. ..QV..SDLV NEEA..Q.H
```

Rn-Subdomain

```
              1                              ▼
SP1R1n Con   LETPKPSISS SNLNPREXME AVSLTCDPET PDASYLWWMN GQSLPMTHXL
SP1R2n Con   PKL...Y.TI N......NKD VLXF..E.KS ENYTTI..L. .....VSPRV
hCEA   IA    P.L....... N.SK.V.DKD ..AF..E... Q..T....V. N....VSPR.
hCEA   IIA   A.P...F.T. N.S..V.DED ..A...E..I QNTT....V. N....VSPR.
hCEA   IIIA  A.L....... N.SK.V.DKD ..AF..E..A QNTT....V. G....VSPR.
hNCA   IA    P.L....... N.S..V.DKD ..AF..E..V QNTT....V. .....VSPR.

51                 ▼
SP1R1n Con   QLSETNRTLF LXGVTKYTAG PYECEIRNPV SASRSDPVTL NLL
SP1R2n CoN   KRPIE..I.I .PS..RNET. ..Q....DRY GGI........ .V.
hCEA   IA    ...NG....T ..N..RNDTA S.K..TQ... ..R...S.I. ...
hCEA   IIA   ...ND....T .LS..RNDV. ....G.Q.EL .VDH....I. .V.
hCEA   IIIA  ...NG....T ..N..RND.R A.V.G.Q.S. ..N....... DV.
hNCA   IA    ...NG.M..T .LS.KRND.. S.....Q..A ..N....... .V.
```

Rc-Subdomain

```
              1                    ▼
SP1R2c Con   YGPDLPRIYP SFTYYRSGEN LYLSCFADSN PPAQYSWTIN GKFQLSGQKL
hCEA   IB    ....A.T.S. LN.S...... .N...H.A.. ...Q...FV. .TF.Q.T.E.
hCEA   IIB   ....D.T.S. .Y....P.V. ..S...H.A.. ...Q...L.D .NI.QHT.E.
hCEA   IIIB  ....T.I.S. PDSS.L..A. .N...HSA.. ..SPQ...R.. .IP.QHT.V.
hNCA   IB    ....V.T.S. .KAN..P... .N...H.A.. ...Q...F.. .T..Q.T.E.

51           ▼
SP1R2c Con   FIPQITTKHS GLYXCSVRNS ATGKESSKSM TVEVS
hCEA   IB    ...N..VNN. .S.T.QAH.. D..LNRTTVT .IT.Y
hCEA   IIB   LLSN..E.N. ...T.QAN.. .S.HSRTTVK .IT..
hCEA   IIIB  ..AK..PNNN .T...F.S.L ...RNN.IVK SIT..
hNCA   IB    ...N..VNN. .S.M.QAH.. ...LNRTTVT MIT..
```

FIGURE 11

PREGANCY SPECIFIC PROTEINS APPLICATIONS

The United States Government has rights in this invention by virtue of National Institute of Health funding Grant No. HD21793.

This is a continuation in part of U.S. Ser. No. 07/298,638 entitled "Pregnancy Specific Proteins" filed Jan. 18, 1989 by Wai-Yee Chan.

BACKGROUND OF THE INVENTION

The present invention generally relates to proteins, particularly a group of pregnancy-specific $\beta$-1 glycoprotein-like proteins, the genes encoding them, and methods for their use.

Pregnancy-specific $\beta$-1 glycoprotein (SP1) is found in the serum of pregnant women and has been isolated in pure form, as reported by Tatarinov and Masyukevich, *Bull. Exo. Biol. Med.* 69, 66–68 (1970). It is synthesized by the syncytiotrophoblast of the placenta and secreted into maternal serum, as studied by Bohn, *Placental Proteins*, pp. 71–18, A. Klopper and T. Chard, editors (Springer Verlag, N.Y. 1979), becoming detectable during the first two to three weeks of pregnancy and increasing as pregnancy progresses to levels of about 200 to 400 $\mu$g/ml, as reported by Tatarinov and Masyukevich *Bull. Exp. Biol. Med.* 69, 66–68 (1970) and Lin, et al., *J. Clin. Invest.* 54, 576–582 (1974).

Even though the placental origin of human SP1 is well established, low levels of this protein can be detected in serum of the normal male and female by radioimmunoassay. The extraplacental source of human SP1 has not been identified. Ectopic production of SP1 by cultured human skin fibroblasts and normal brain cells has been reported by Heikinheimo, et al., *J. Clin. Endocr. Metab.* 51, 1432–1436 (1980); Rosen, *Pregnancy Proteins*, pp. 223–234 (1982); and Chou, *Oncodevelop. Biol. Med.* 4, 319–326 (1983), but the cause is not known.

As first reported by Bohn, *Blut* 24, 292–302 (1972), SP1 isolated from placenta consists of a single polypeptide chain with an N-terminal histidine, having a molecular weight of 90,000, of which 30% is carbohydrate. Several subsequent studies have indicated that this "protein" is actually a heterogeneous mixture of several components. There is a wide discrepancy of reported molecular weights for human placental SP1. Values determined by gel filtration, ultracentrifugation and SDS-PAGE vary from 110,000 to 42,300, respectively. Carbohydrate varies from 28 to 32%. As reviewed by Bischof, *Contri. Gynecol. Obstet.* 12, 6–92 (1984), electrophoretic mobility ranges from $\alpha$, $\beta$, to gamma. Genetic variants of SP1 have also been reported in both normal and abnormal pregnancies as well as in tumors. It has been suggested that these variants involve a change in protein size or sequence.

cDNA sequences encoding placenta-specific SP1, having slight differences in sequence at the 3' end, were reported by Watanabe and Chou in *J. Biol. Chem.* 263, 2049–2056 in 1988, and Streydio, et al. in *Biochem. Biophys. Res. Comm.* 154(1), 130–137, (1988). Monoclonal antibodies to human SP1 have also been reported to have different and unique specificities and affinities, although it is not known if the antigenic determinants are on the same or different proteins.

SP1 determinations have great potential clinical application, even though the function of SP1 is still not known. The medical relevance of SP1 in a number of situations has been extensively investigated. The most important use of SP1 is for monitoring various conditions, both normal and pathological, during pregnancy, reviewed by Bischof (1984). SP1 measurements have also shown promise for the diagnosis and monitoring of trophoblastic and some nontrophoblastic tumors, as described by Sorensen, *Clin. Chim. Acta* 121, 199–208 (1984).

Despite the potential, SP1 has not been well utilized in clinical medicine because of the lack of reliable quantitation methods. At present, the majority of the SP1 assays depend on antiqen-antibody interaction, dependent on the nature of the SP1 molecule and on the specificity of the antibody involved. Heterogeneity of the SP1 molecules decreases the reliability of these immunoassays.

It is therefore an object of the present invention to provide the nucleotide sequences and structure of a group of several SP1 proteins.

It is a further object of the present invention to provide a method and means for producing extremely pure SP1 proteins for pharmaceutical use.

It is another object of the present invention to provide a methods and means for producing monoclonal antibodies for quantitating the different species of SP1 and for improving assays for CEA by eliminating cross-reactions with SP1-like proteins in non-placental tissues.

It is a further object of the present invention to provide methods and means for use in pregnancy assays and in detection and monitoring of trophoblastic and some non-trophoblastic tumors It is still another object of the present invention to provide reagents for use in preventing fetal rejection, in inducing rejection of the embryo in therapeutical procedures, and in improving the transfer of immunoglobulins into the fetus.

SUMMARY OF THE INVENTION

At least seven genes have been identified which encode proteins generally identified as pregnancy specific protein (SP1), also known as pregnancy specific beta glycoprotein (PSBG). These genes have been found using human placental SP1 labelled cDNA in a number of mammalian species, including human, baboon, cow, sheep, goat, pig and rat, and non-mammalian species, including fish and bird. These genes can be classified as those specifically found in human placenta (which can be grouped by the presence or absence of specific restriction enzyme sites and hydrophobic regions into at least three groups); in intestinal cells; in cells of both testis and placental origin; in tissue of testis origin; and in HeLa cells.

An exemplary clone of the first group of placental specific SP1-like proteins is hPS12. A clone encoding a SP1-like protein which is specifically found in placenta and which appears to have a hydrophobic C-terminal region, indicating that it is membrane bound, is hPS2. Another clone having a sequence found in placenta is hPS11, which is very closely related to clone PSG16 of Watanabe and Chou, *J. Biol. Chem.* 263 (4), 2049–2056 (1988), and clones PSBGC and PSBGD of Streydio, et al., *Biochem. Biophys. Res. Comm.* 154(1), 130–137 (1988). Clones isolated from an intestinal library include hIS1, hIS2 and hIS3. A clone common to both placenta and testis is hPS3. Clones isolated from a testis cDNA library include hTS1, hTS2 and hTS3. Clones isolated from a HeLa cell library include hHS1, hHS2, hHS8, hHS11, hHS4, hHS3, hHS6, hHS9, hHS12, and hHS14.

These cDNAs are at least 65% homologous with some members of the immunoglobulin gene superfamily such as Carcinoembryonic Antigen (CEA). The proteins encoded by the cDNA of intestinal cell origin appear to be more closely related to the CEA proteins than to the other SP1 proteins.

Methods for making and using the DNA sequences, proteins, and antibodies to the proteins are also described, particularly for diagnostic work, as in making and purifying reagents for use in pregnancy assays, in detection and monitoring of trophoblastic and some non-trophoblastic tumors and in purification of reagents used to assay for SP1 and for CEA.

Immunosuppressive activity and growth promoting activities have been demonstrated by suppression of lymphocyte proliferation and inducement of megakaryocytopoiesis, respectively.

BRIEF DESCRIPTION OF THE DRAWINGS

FIG. 2 is the nucleotide and predicted amino acid sequence of hPS11. The amino acid numbers are above and nucleotide numbers below the sequence. Potential glycosylation sites are underlined. Deduced amino acid sequences identical to that of tryptic fragments of the pure protein are boxed. (∇) Amino acid residue different from those determined by amino-terminal analysis of pure SP1; (▼) cysteine residues; (***) stop codon. The ends of the different subdomains are indicated by R1n, R2n, and R2c.

FIG. 3 is the nucleotide sequence and predicted amino acid sequence of hPS2. Nucleotide numbers are indicated. Potential glycosylation sites are underlined. Open inverted triangles indicated conserved Cys residues. Solid squares indicated polyadenylation sites. * indicates stop codon. Boundaries of the different domains are indicated by: N, N-terminal domain; Rn, n-subdomain of repeat unite; Rc, c-subdomain of repeat unit; C, C-terminal domain.

FIG. 4 is the nucleotide sequence and predicted amino acids of hPS12 and the 5' extended sequence derived from hPS90. The nucleotide numbers are indicated. Potential glycosylation sites are underlined. Open inverted triangles indicate conserved Cys residues. Solid squares indicate polyadenylation site. * indicates stop codon. Boundaries of the different domains are indicated by: N, N-terminal domain; Rn, n-subdomain of repeat unite; Rc, c-subdomain of repeat unit; C, C-terminal domain.

FIG. 5 is the nucleotide sequence and the derived amino acid sequence of hPS3. The nucleotide numbers are shown beneath the sequence. The potential glycosylation sites are underlined. The amino acid sequence determined by protein sequencing is boxed (Peptide C).

FIG. 6 is a comparison of the nucleotide sequence of the 3' EcoRI fragment of hTS1 with hPS11.

FIG. 7 is the nucelotide sequence of hTS16. Number is the nucleotide base number. Amino acids encoded by exons are shown. Polyadenylation signal sequence is scored by a broken underline. Potential glycosylation sites are underlined and conserved cysteine residues are boxed. Large empty triangle indicates deletion. Boundaries of exon/intron and domain regions are shown. IVS: intervening sequence; N: N-terminal region; Rn: n-subdomain; Rc: c-subdomain; C: C-terminal domain.

FIG. 8 is the nucleotide sequence and derived amino acid sequence of hHS2. The nucleotide numbers are indicated. Potential glycosylation sites are underlined. Cysteine residues are boxed. The boundaries of the different domains are marked: N-Term (N-terminal domain), R1n (n-subdomain of repeat 1), R2n (n-subdomain of repeat 2).

FIG. 9 is the nucleotide sequence and derived amino acid sequence of hIS1. Nucleotide numbers are indicated. Potential glycosylation sites are underlined. Cysteine residues are boxed. The boundaries of different domains are marked: N-Term (N-terminal domain), R1n (n-subdomain of repeat 1), R1c (c-subdomain of repeat 1). (▼) indicates potential signal peptidase cleavage point.

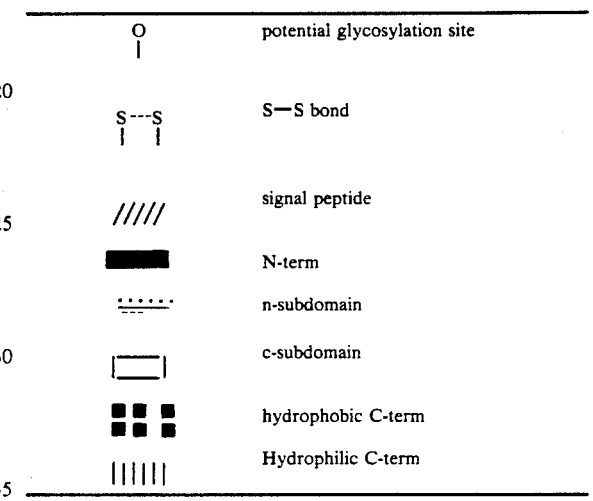

FIG. 11 is a comparison of the aligned consensus amino acid sequences encoded by human placental SP1 cDNAs with that encoded by human CEA and normal crossualting antigen (NCA) cDNAs. Potential glycosylation sites are underlined. Solid inverted triangles indicate conserved Cys residues. Amino acids are numbered with reference to the beginning of each domain or subdomain. SP1 NCon, Consensus sequence of N-terminal domain of SP1 cDNAs; SP1R1nCon, consensus sequence of R1n-subdomain of SP1 cDNAs; SP1R2cCon, consensus sequence of R2c-subdomain of SP1 cDNAs. Domain notation of CEA and NCA is the same as in published references.

Figure 12:
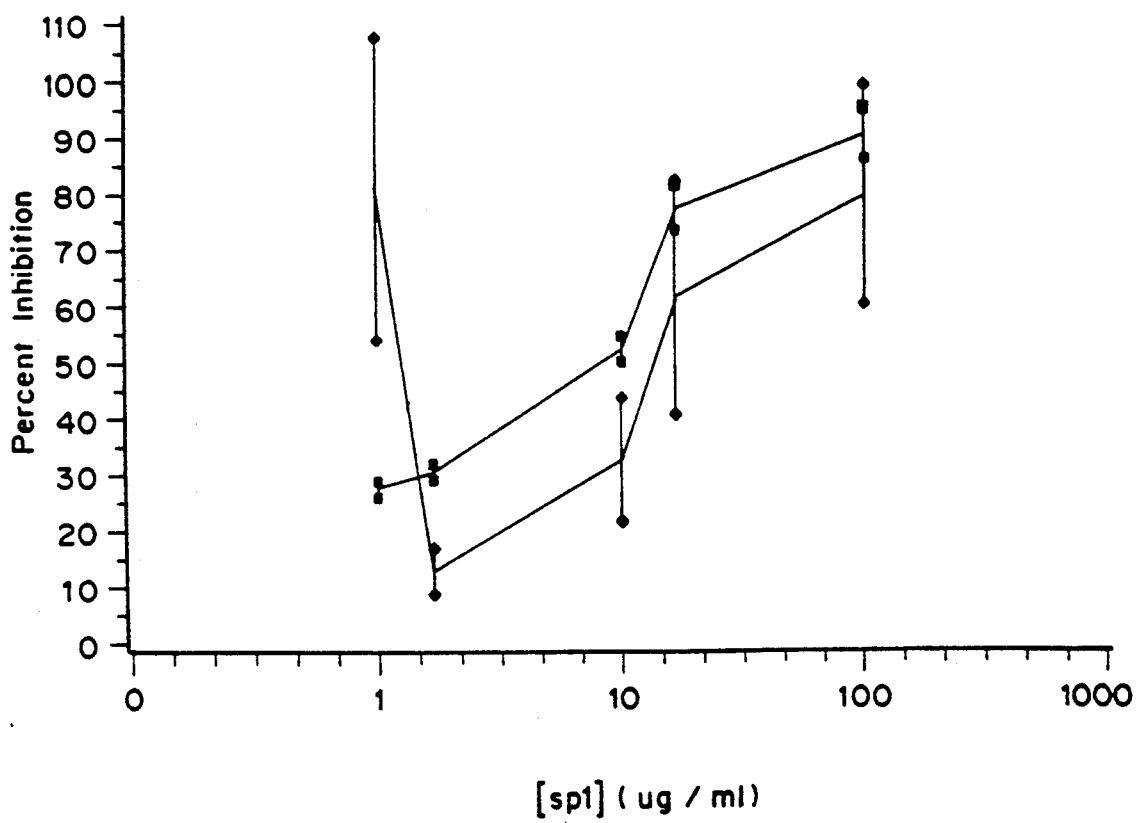

FIG. 12 is a graph of the immunosuppressive activity of human placental SP1, plotting percent inhibition of mixed lympohocyte reaction versus SP1 (micrograms per ml).

Figure 13:
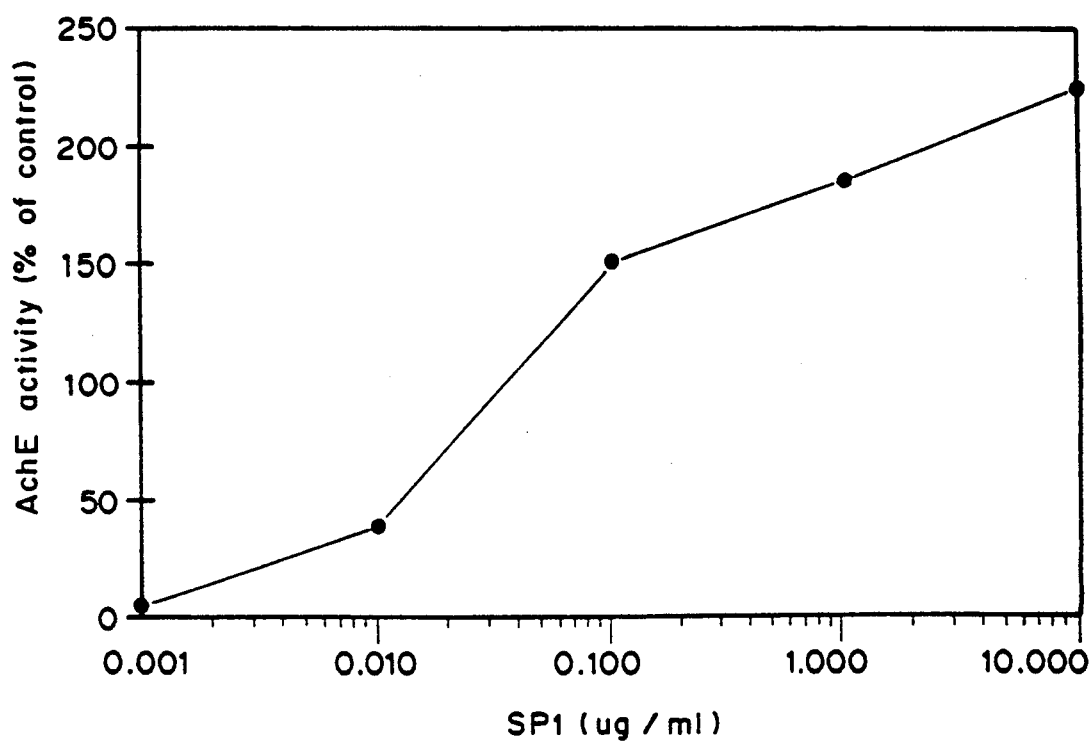

FIG. 13 is a graph of the growth promoting activity of human placental SP1, plotting % murine megakaryocyte acetylcholinesterase activity of the control versus SP1 (micrograms per ml).

DETAILED DESCRIPTION OF THE INVENTION

Several new activities, including growth factor activity and immunosuppressive activity, for SP1 proteins have now been determined, based on the structure and sequence of the cDNA clones described in U.S. Ser. No. 07/298,638, and confirmed in vitro. Conservation of the genes encoding these proteins has also been demonstrated in a number of mammalian and non-mammalian species, indicating the basic importance of the proteins, and establishing the utility of several animal species as models for further studies.

U.S. Ser. No. 07,298,638 describes the isolation and characterization of cDNA clones encoding several distinct, but closely related, proteins. At least seven genes are identified which encode proteins specifically found in placenta (which can be grouped by the presence or absence of specific restriction enzyme sites and hydrophobic regions into at least three groups), genes found in intestinal cells, genes found in cells of both testis and placental origin, genes found only in tissue of testis origin, and genes found in HeLa cells. An exemplary clone of the first group of placental specific SP1-like proteins is hPS12. A clone encoding a SP1-like protein which is specifically expressed in placenta and which appears to have a hydrophobic C-terminal region, indicating that it is membrane bound, is hPS2. Another clone having a sequence expressed in placenta is hPS11, which is very closely related to clone PSG16 of Watanabe and Chou, J. Biol. Chem. 263 (4), 2049–2056 (1988), and clones PSBGC and PSBGD of Streydio., et al., Biochem. Biophys. Res. Comm. 154(1), 130–137 (1988). Clones isolated from an intestinal library include hIS1, hIS2 and hIS3. A clone common to both placenta and testis is hPS3. Clones isolated from a testis cDNA library include hTS1, hTS2 and hTS3. Clones isolated from a HeLa cell library include hHS1, hHS2, hHS8, hHS11, hHS4, hHS3, hHS6, hHS9, hHS12, and hHS14. These cDNAs are at least 65% homologous with some members of the immunoglobulin gene superfamily such as Carcinoembryonic Antigen (CEA). Important features of these proteins are the similarities in the occurrence of β-sheet and repeating domain structure, and conserved glycosylation sites and cysteine residues within the repeating domains, indicating that they all evolved from the same primordial gene by gene duplication or exon shuffling. The CEA family differs from the SP1 family by having a high degree of glycosylation. The proteins encoded by the cDNA of intestinal cell origin appear to be more closely related to the CEA proteins than to the other SP1 proteins.

Several uses of the DNA sequences, proteins, and antibodies to the proteins are also described in Ser. No. 07/298,638, particularly for diagnostic work, as in purifying reagents for use in detecting CEA.

Several cDNA clones for SP1 proteins have been isolated and characterized. Some are analogous to previously reported cDNAs for SP1 proteins. The SP1 genes of the present invention include the cDNA sequences described in the figures and examples, homologous sequences thereof isolated from any naturally-occurring genome, and any analog thereof in which nucleotides in the sequence are substituted, deleted or added while encoding a protein having at least a portion of the specific biological activity or unique structure of the encoded peptide. The present invention also includes a substantially pure peptide or protein as described in the figures and examples, or as expressed from the described cDNAs, analogues thereof in which amino aids in the sequence are substituted, deleted or added while maintaining at least a portion of the specific biological activity or structure of the peptide, and conjugates of any such peptide or analog.

For purposes of clarification, the following nomenclature is used herein to describe the cDNA clones:

cloning vector: lambda, lambda phage; p, plasmid; m, M13 phage lower case letter indicating species of origin of cDNA: h, human; r, rat; b, bovine Capital letter indicating tissue of origin of cDNA: P, placenta; I, intestine; H, HeLa cells; T, testis Capital letter indicating protein family, here, S indicates the SP1 protein family clone number .subclone number In some cases, clones have previously been referred to in the literature by a different reference number. For example, hPS11 has been referred to as hPSP11. hHS2 has been referred to as hHSP2. hPS11 is analogous to the clone described by Watanabe and Chou, J.Biol.-Chem. 263(4), 2049 (1988), PSG16, and that by Streydio, et al., Biochem. Biophys. Res. Comm. 154(1), 130–137 (1988), PSBGC and D.

hPS11 is an example of one of the clones of the present invention encoding a placental SP1-like protein that is detected in placenta and in testis. The amino-terminal 143 amino acids of hPS11, besides having a characteristic secondary structure, appears to constitute a specific domain of the protein containing three of the seven glycosylation sites. The rest of the protein is composed of repeating units. There are two internal repeats, R1n and R2n, each of 279 bp, encoding 93 amino acids, that are identical in 73% of their nucleotides and 48% of their amino acids. The glycosylation sites of the repeats are not conserved. The second repeat is more hydrophilic than the first repeat. After the internal repeats there are 90 amino acids before the stop codon TGA, designated R2c. This region contains no glycosylation sites.

Figure 1:
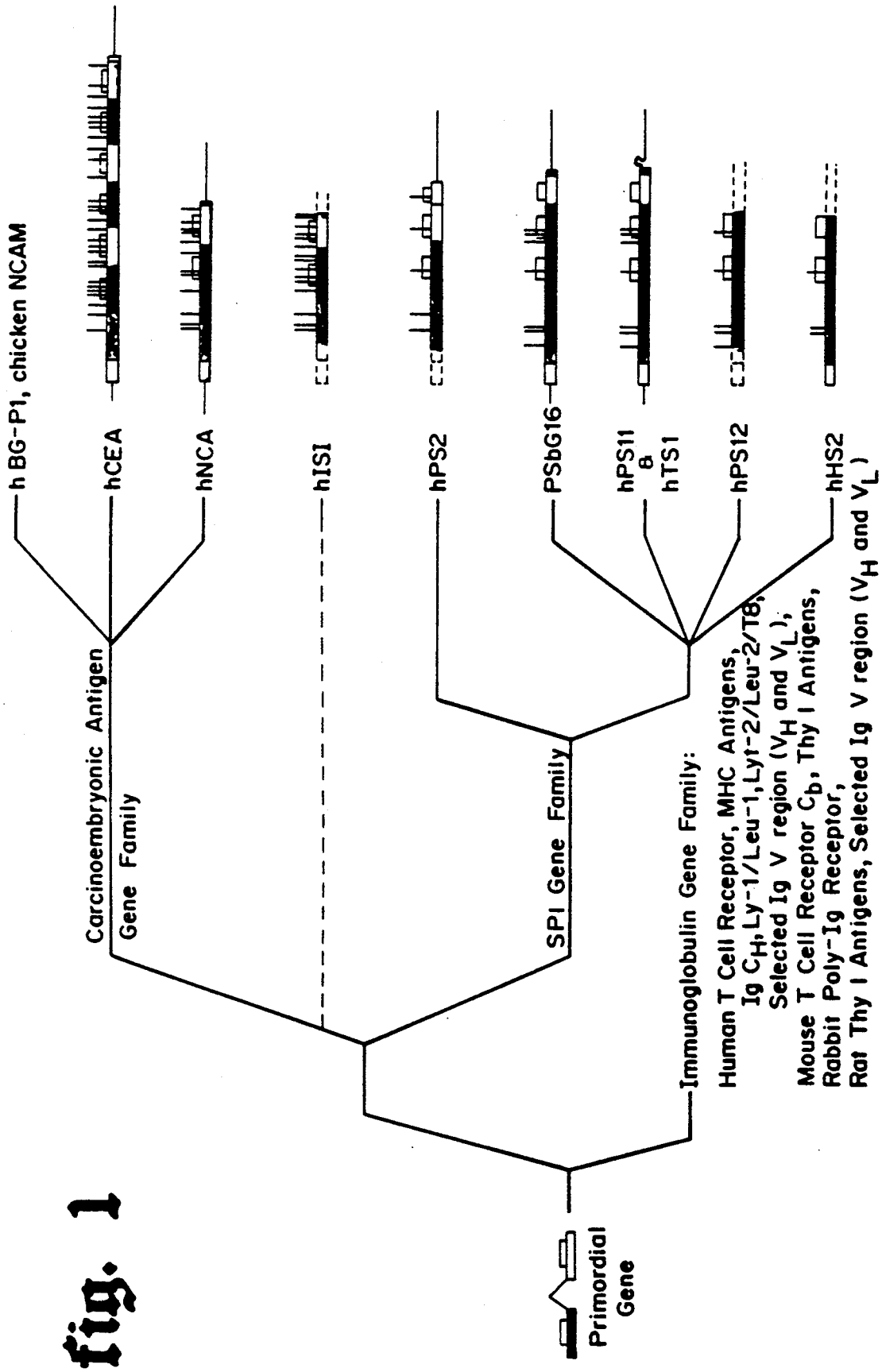
FIG. 1 summarizes the relationship between the SP1 genes, CEA and the immunoglobulin gene superfamily.

It is believed that the SP1 family was formed by duplication of a primordial gene, which developed into the SP1 genes, the Carcinoembryonic Antigen genes, and the immunoglobulin genes. The relationship is depicted in FIG. 1. One characteristic of the members of the SP1 gene family is the deletion of the c-subdomain of the first repeating unit (R1c) in several of the cDNAs cloned, indicating that hPS11, hPS12, pSG16 and hHS2 all originate from one ancestor which contains two of the repeating units with one c-subdomain deleted. hIS1, even though discovered by hybridization with an SP1 probe, is closer to the CEA family than the SP1 family, and may therefore be intermediate between the two families of genes.

Besides having immunosuppressive function, CEA is believed to be involved in cell-cell interaction and growth factor like activities. SP1 proteins, especially those in the group isolated from an intestine gene library, are expected to have analogous functions.

SP1 genes and immunoglobulin genes have similar overall domain structure, conserved disulphide bridges and β-sheet structure and approximately 65% homology in some part of their nucleotide sequence. This relationship has a very important implication as to the function of SP1 proteins. Many immunoglobulin gene family members have receptor or cell recognition functions, suggesting that SP1 might also have similar physiological roles. The similarity in structure between the MHC antigen and the membrane bound form of SP1 specific to placenta (hPS2) suggests that SP1 might compete with the MHC antigens in presentation of the fetal antigens to killer T cells. If so, SP1 may prevent fetal allograft rejection by blocking the action of MHC antigens and killer T cells and provide local immunity to the implanted embryo. The similarity in structure between the poly Ig receptor and the cytoplasmic form of SP1 (hPS11 and hPS12) suggests that SP1 might have functions similar to that of poly Ig receptor, i.e., transcellular transfer of immunoglobulins from the mother to the fetus.

cDNA clones encoding genes for each of the several groups of SP1-like proteins have been isolated and characterized, as described in the following non-limiting examples. It is understood that specific cDNA sequences can be modified by those skilled in the art, for example, by labelling, fusion with regulatory sequences, insertion into expression vectors, and substitution or deletion of nucleotides encoding specific amino acids, without departing from the scope of the nucleotide and amino acid sequences of the present invention, and the methods for their use.

The methods and compositions of the present invention are further illustrated by the following non-limiting examples, using the methods and reagents described below.

Vector libraries used in the examples and which are suitable for use in the present invention are sold by Clontech Laboratories, Palo Alto, Calif., or may be prepared in accordance with known procedures, such as those described in "Construction and Screening cDNA Libraries in lambda gt10 and lambda gt11", *A Practical Approach, DNA Cloning* (IRL Press, Oxford, England, 1985) Vol. 1, pp. 49-79. A lambda gt11 human placental expression library obtained from M. D. Anderson Hospital and Tumor Institute was used in examples of the present invention. This library includes double-strand cDNA with over 500 base pairs (bp), cloned into the EcoRI site of the lambda gt11 phage.

Genes isolated from the library can be expressed by plating $2 \times 10^6$ phages from a human placental lambda gt11 library on *E. coli* Y1090 at a density of $5 \times 10^5$ plaques per 150 mm L-agar plates and inducing expression by adding IPTG. *E. coli* Y1090 contains: lac repressor which prevents lacZ-directed gene expression until it is derepressed by the addition of IPTG (Isopropyl-$\beta$-D-thiogalactopyranoside) to the medium; a deficiency in the lon protease which increases the stability of the recombinant fusion protein; and supF to suppress the phage mutation causing defective lysis. To ensure that fusion proteins toxic to the host produced by particular recombinants will not inhibit the growth of particular members of the library, plaque formation is initiated without expression from the lacZ gene promoter. After the number of infected cells surrounding the plaques is pin-size, lacZ-directed gene expression is switched on by the addition of IPTG. The production of the protein from the plaque is induced by overnight incubation at 42° C. in the presence of IPTG.

It is preferable to plate out only a sufficient number of the sequence-carrying vectors to proportionally represent groups of sequences found in the library. This can be accomplished by following the procedure in *Genetic Engineering*, Vol. 1 (Academic Press, New York 1981).

In order to detect the desired protein, a filter is contacted with the expressed proteins in an agar plate, so that the proteins adhere to the filter. The filter is prehybridized so that the antibodies will not bind non-specifically to the filter. The filter is then incubated in a labeled antibody solution and an autoradiogram made. The DNA encoding the proteins complexing with the marked antibody are identified by superimposing the marked autoradiogram over the agar plate. Antibody against SP1 protein is commercially available from Calbiochem of San Diego, Calif. This antibody is raised in rabbit, adsorbed with other placental proteins and affinity purified. The antibody (100-150 $\mu$g) is labeled with 1 mCi of $^{125}$I in the presence of iodogen (1,3,4,6-tetrachloro-3$\alpha$, 6$\alpha$-diphenylglycouril) from Sigma Chem. Co. of St. Louis, Mo., and 1M Tris-HCl, pH 8.0.

The SP$_1$ protein antibody can bind to proteins which are selected members or fragments of members of SP$_1$ proteins. The antibody-protein complex is identified by autoradiography which detects the radioactivity of the labeled antibody. The autoradiogram then is disposed over the agar dish in the same position as that of the filter which was originally used to adsorb the proteins. In this manner, the phage containing the insert producing the marked protein can be identified.

Once the appropriate phages are identified, the *E. coli* colonies containing those phages are cut out of the agar, and placed in a microfuge tube with 0.5 ml of L-Broth. The suspension is vortexed to break up the agar and release the phage from the *E. coli* colony. The supernatant portion of the L-Broth containing the phages is replated on *E. coli* Y1090 at a density of $5 \times 10^5$ plaques per 150 mm L-agar plates. The previous procedure of dispersing the phages, treating the proteins expressed by the DNA contained within the phages with an antibody and identifying the phages carrying the DNA fragments of interest, as previously described, is repeated until all phages in the agar plate contain DNA that express proteins which react with the antibody. A 10 mM solution of Tris-Hcl, pH 7.5, containing 20 mM magnesium chloride is added to agar plate and the phages allowed to diffuse from the agar into the solution for two hours. The solution containing the phages is then withdrawn from the agar plate.

The cDNA screening process is carried out by exposing the autoradiogram to radiolabeled DNA probe, under conditions which promote DNA hybridization. The DNA probe is characterized by a nucleotide sequence that is complementary to at least a portion of the nucleotide sequence of a DNA fragment coding for the selected member of the SPI family of related proteins.

Enzymes and Chemicals

*E. coli* DNA polymerase 1 and T4 polynucleotide kinase were purchased from Boehringer Mannheim Biochemicals, Indianapolis, Ind. DNAse 1 was purchased from Pharmacia, Piscataway, N.J. All restriction enzymes were supplied by either Bethesda Research Laboratories, Gaithersburg, Md., or New England Biolab, Beverly, Mass. LambdaSorb phage adsorbent was purchased from Promega Biotec, Madison, Wis. The Phage Lambda Mapping Quik-Kit was supplied by Collaborative Research, Inc., Bedford, Mass. Nylon filters for library screening and radiochemicals including $\alpha$ and gamma $^{32}$P deoxynucleotides were purchased form Amersham, Arlington Heights, Ill. Nitrocellulose filters were supplied by Schleicher & Schuell, Keene, N.H. Highly purified human placental genomic DNA was purchased from Sigma, St. Louis, Mo. All other chemicals were reagent or molecular biology grade.

EXAMPLE 1

Isolation and Characterization of cDNA Encoding a Cytoplasmic Form of Placental SP1 cDNA clones SP1 proteins were isolated from a group of fifteen positive clones obtained by screening a human placental cDNA library, initially with SP1 protein antibody and then with a partial SP1 cDNA probe, described by Chan, et al., in *Human Reproduction* 3(5), 677-685 (1988). The cDNA insert was released from a lambda gt11 vector by complete and partial digestion with EcoRI and subcloned into M13mp18 and M13mp19. The DNA sequence was determined by a modified dideoxy chain termination method using Klenow fragment at 50° C. or Sequenase from USB, Cleveland, O.H., at 37° C., as described in L. Johnston-Dow et al., *BioTechnicues* 5,754-765 (1987). M13 universal sequencing primer (Pharmacia, Piscataway, N.J.) as well as synthetic oligonucleotide primers were used to prime the sequencing reaction. All sequences were determined three or more times as well as from different M13 subclones. Subclones of opposite orientation, identified by the C-test as described by J. Messing, *Methods of Enzymology* 101C, pp. 20-77, R. Wu et al., eds. (Academic Press, New York 1983), were sequenced so that the final sequence was determined from both strands. DNA sequences were analyzed by the Sequence Analysis Software Package of the Genetics Computer Group at the University of Wisconsin as described in H. Devereux et al., *Nucl. Acid Res.* 12, 387-395 (1984).

Each clone was Southern blot analyzed and sized and placed into one of three groups. The DNA was digested to completion with EcoRI. The digested DNA fragments were separated by electrophoresis on 1% agarose in 1×TA buffer (40 mM Tris base, 20 mM sodium acetate, 18 mM sodium chloride, 1 mM disodium EDTA, pH 8.0), and transferred to a nitrocellulose filter as described by Smith in *Anal. Biochem.* 109, 123-129 (1980). Blots were analyzed with cDNA inserts previously labeled with $^{32}P$ by nick translation as described by Rixon, et al., in *Biochemistry* 21, 3237-3244 (1983). Hybridization and washing conditions were as described by Kan, *Proc. Natl. Acad. Sci. USA* 75, 5631-5635 (1978). Hybridization and washing use high stringency conditions, with 2×SSC at 65° C. for 15 minutes and repeated, 2×SSC containing 0.1% sodium dodecylsulfate at 65° C. for 30 minutes and 0.1×SSC at 65° C. for 10 minutes, as recommended by the manufacturer of the filters. Under these conditions only the highly homologous cDNAs are identified. When nylon filters were used instead of nitrocellulose, the procedures were modified as recommended by the manufacturer (Amersham, 1985). Nylon blots were washed twice with 2×SSC (0.3M sodium citrate, 0.3M sodium chloride) at 65° C. for 15 minutes, twice with 0.1×SSC-0.1% SDS at 65° C. for 30 minutes and once with 0.1×SSC at 65° C. for 30 minutes.

For genomic DNA analysis, human placental genomic DNA predigested with EcoRI, BamHI and BamHI/HindIII was purchased from Oncor, Inc., Gaithersburg, Md. Twelve micrograms of each type of DNA were separated by electrophoresis through 0.8% agarose and Southern blotted.

Clones were divided into three groups. Group 1 clones had cDNA inserts with no internal EcoRI site, and a length of no longer than 1720 bp (base pairs) hPS12 is a representative clone. Group 2 clones had cDNA inserts with one internal EcoRI site, and a length of no longer than 1958 bp with EcoRI fragments of 622 and 1336 bp. hPS11 is a representative clone. Group 3 clones had cDNA inserts with two internal EcoRI sites, and a length of no longer than 2215 bp with EcoRI fragments of 450, 645 and 1120 bp. hPS2 is a representative clone.

Clones not having internal EcoRI sites because they were less than full length were assigned to the appropriate group based on their restriction enzyme maps or nucleotide sequences. The hybridization of cDNA inserts of all three groups with the probe under highly stringent condition indicated that they were highly homologous to the SP1 probe.

The nucleotide sequences of the cDNA insert of the six clones in group 2 were determined by Sanger's dideoxy chain termination method, as described in the Amersham (1985) cloning and sequencing manual. The DNA sequences were analyzed by the computer programs described in *Nucleic Acids Res.* 12, 605-614 (1984). The nucleotide sequence for hPS11, which is expressed in placental tissue, is set out on the lower series of lines in FIG. 2. The peptide sequence of hPS11 is shown in the top series of lines in FIG. 2, with each amino acid residue positioned directly above the sequence of DNA bases that codes for it.

Amino acid sequences identical to those of two tryptic fragments of pure SP1 protein, prepared according to Chan, et al., in *Human Reproduction* 3(5), 677-685 (1988), are present in the coding sequence of hPS11, establishing the identity of this cDNA with purified SP1 protein. Purified human SP1 protein (1 mg/ml) was incubated with trypsin (L-1-tosylamido-2-phenylethylchloromethyl ketone) TPCK-treated, final concentration of 10 μg/ml in 50 mM ammonium bicarbonate, pH 8, at 37° C. for 16 hours. The tryptic fragments were then separated by HPLC using a reverse-phase C18 column, equilibrated with 0.05% trifluoroacetic acid (TFA). Peptides were eluted from the column by an acetonitrile gradient of 0-40% in 80 minutes at a flow rate of 1 ml/min. Fractions of 1 ml were collected. Peptide peaks were randomly selected and concentrated for further purification on the same column. The procedure for rechromatography was as follows: 0% for 10 minutes, 1 ml/min; 0-20% for 20 minutes, 1 ml/min; 20% constant for 60 minutes, 0.5 ml/min. The amino acid sequences of randomly selected tryptic peptides "B" and "C" were determined by the method described by Edman and Begg, in *Eur. J. Biochem.* 1, 80-91 (1967) in a gas phase sequenator as described in *Proc. Natl. Acad. Sci. USA* 82, 3616-3620 (1985) and using polybrene as a non-protein carier. About 0.2-0.5 nmol of peptide were applied to the gas phase sequenator. Phenylthiohydantoin (PTH) derivatives from the sequenator were identified by HPLC using a waters Nova Pak C18 column as described in *J. Biol. Chem.* 261, 14335-14341 (1986). Norleucine was added to each sample as an internal standard. All PTH derivatives were monitored at 265 nm and 313 nm for serine and threonine, respectively. These sequences are boxed in FIG. 2.

The hPS11 cDNA has 1958 bp with a 5' non-coding sequence of 73 bp and an open reading frame encoding a protein of 419 amino acids with a calculated molecular mass of 47.2 kDa. Even though no upstream stop codon can be identified, the sequence around the presumed translation initiation codon ACCATGG agrees with the consensus sequence for initiation of translation in vertebrates as suggested by M. Kozack, *Nucl. Acid Res.* 15: 8125-8148 (1987). Amino-terminal analysis of pure SP1 protein demonstrates a sequence of N—X—Thr—Ile—Glu—Ala—Gln—Pro—Pro—Lys—Val—Ser—Glu, corresponding to the predicted amino acids 37-47 of hPS11 except Glu-41 and Thr-43. These differences could be due to the majority of the SP1 proteins having blocked N-terminals, so that this procedure only gave the N-terminal sequence of a minor component of SP1 preparation with unblocked N-terminal. Analysis with the PEPPLOT computer program of the Sequence Analysis Software Package indicated that the N-terminal 34–35 amino acids demonstrate the characteristics of a putative signal peptide having a hydrophobic core, a helix breaker (Pro) and a small uncharged amino acid at the site of cleavage (Ala), as suggested by G. Blobel et al., *J. Cell. Biol.* 67, 835–851 (1975) and T. Yamamoto et al., *Cell* 39, 27–38 (1984).

There are seven possible N-glycosylation sites of the structure Asn-X-Thr/Ser in the predicted amino acid sequence, underlined in FIG. 2. All potential glycosylation sites are present within the N-terminal three-fourths portion of the protein. Analysis of the predicted secondary structure with the computer algorithm of B. A. Jameson et al., *CABIOS* 4: 181–186 (1988) shows that the protein is in the form of beta-sheets except for two small areas near the N-terminal (amino acids 35–50 and 160–170), which are in the form of alpha-helices. With the PEPPLOT computer program, it is possible to determine that the protein is largely hydrophilic, except for the amino-terminal 10 amino acids The amino-terminal 143 amino acids, besides having a characteristic secondary structure, appears to constitute a specific domain of the protein containing three of the seven glycosylation sites. Analysis with the REPEAT program indicates that the rest of the protein is composed of repeating units. There are two internal repeats, each of 279 bp, encoding 93 amino acids. R1n starts at nucleotide 503 (Leu-144) and runs through 781 (Leu-236). R2n starts at nucleotide 782 (Pro-237) and runs through 1060 (Leu-329). These two repeats are identical in 73% of their nucleotides and 48% of their amino acids. There is only one potential glycosylation site in the first repeat in contrast to the second repeat which has three glycosylation sites. The glycosylation sites of the repeats are not conserved. The two cysteine residues in the repeats are conserved and both are separated by 47 amino acids in their respective domains. The second repeat is shown to be more hydrophilic than the first repeat upon analysis of the predicted amino acid sequence with the PEPPLOT program.

After the internal repeats there are 90 amino acids before the stop codon TGA. This region, designated R2c, begins with nucleotide 1061 (Tyr-330) and continues through 1315 (Ser-414), and contains no glycosylation sites. There are two cysteine residues 39 amino acids apart. There is 655 bp of 3' non-coding sequence following the stop codon.

EXAMPLE 2

Isolation and Characterization of cDNA Encoding an Apparently Membrane Bound Form of Placental Specific SP1

Clone hPS2, expressed uniquely in placenta and containing two internal EcoRI sites, was sequenced and characterized as described in Example 1. This clone represented partial cDNA with an incomplete 5' coding sequence. To obtain more 5' sequence, the most 5' EcoRI-BamHI fragment of hPS2 was used as a probe to rescreen the same cDNA library. No more 5' sequence was found.

The nucleotide and predicted amino acid sequence of hPS2 is shown in FIG. 3. It has 1744 bp with an open reading frame of 1053 bp encoding 351 amino acids, a stop codon TGA, and a 3' non-coding sequence of 659 bp with the polyadenylation signal ATTAAA 14 bp upstream from a 29 bp poly(A) tail.

The peptide encoded by hPS2, as compared with hPS11 and hPS12, contains part of the N-terminal domain including 92 amino acids that are 91.2% homologous at the nucleotide level and 82.2% homologous at the amino acid level. Two of the three glycosylation sites are also conserved (a total of five potential glycosylation sites in the encoded protein can be identified). The R1n subdomain containing 93 amino acids is 91.3% homologous at the nucleotide level and 82.3% homologous at the amino acid level. When compared to R1n of hPS11, both the glycosylation site and the positions of the cysteine residues are conserved. The c-subdomain has 81 amino acids. As in the n-subdomain, there is 91.3% homology at the nucleotide level and 92.3% homology at the amino acid level. The cysteine residues but not the glycosylation sites are conserved. However, no homology is observed beyond the c-subdomain.

One important difference between the two cDNAs, hPS11 and hPS2, is in the hydrophobicity of their C-terminal regions. The secondary structure of the encoded protein of hPS11, as predicted with the PEPPLOT program, shows the protein to be largely hydrophilic, indicating that it is not a membrane protein. The only hydrophobic part is at the N-terminal 34–35 amino acids which corresponds to the signal peptide. The hydrophobic C-terminal region of hPS2 is comparable with the membrane anchor region of a number of membrane bond proteins including that of CEA and some of the immunoglobulins. Prediction of secondary structure using programs available in the Sequence Analysis Software Package of the Genetics Computer Group also show that the protein is mainly in the form of beta-sheets.

EXAMPLE 3

Isolation and Characterization of cDNA Encoding a Third Type of Placental Specific SP1

FIG. 4 is the nucleotide sequence and the encoded amino acid sequences of hPS12, the clone described in Example 1 as representative of "group 1" placenta-specific SP1-like proteins characterized by no internal EcoRI sites. The open reading frame encodes 395 amino acids, a stop codon and 3' non-coding sequence of 252 bp. hPS12 has only been detected in the placenta.

This clone also represented only partial cDNA, with an incomplete 5' coding sequence. To obtain more 5' sequence, the most 5' EcoRI-BAMHI fragment of hPS12 was used as a probe to rescreen the cDNA library. Two clones, hPS89 and hPS90, with more 5' sequence than hPS12, were identified. The composite cDNA has 1573 bp with a 5' non-coding sequence of 45 bp, an open reading frame of 1272 bp encoding 424 amino acids with a calculated molecular mass of 47.5 kD, a stop codon of TAA and a 3' non-coding sequence of 253 bp. Even though no upstream stop codon can be identified, the sequence around the presumed translation initiation codon ACCATGG agrees with the consensus sequence for initiation of translation in vertebrates as suggested by Kozak, *Nucleic Acid Res.* 15, 8125–8148 (1987). No poly(A) tail was found in any of the hPS12 clones sequenced. Eight potential glycosylation sites, two of the form Asn-X-Ser and six of the form Asn-X-Thr are present. The encoded protein contains an N-terminal doamin, two n-subdomains and one c- domain each containing two conserved Cys residues and a C-terminal domain, as is characteristic of all SP1 proteins reported other than hPS2.

Prediction of secondary structure with the Sequence Analysis Software Package of the Genetics Computer Group show that the protein encoded by hPS12 is mainly in the form of beta sheets. The PEPPLOT program (Goldman, et al., *Ann. Rev. Biophys. Chem.* 15, 321-353 (1986)) and the PLOTSTRUCTURE program (Chou, et al., *Adv. Enzymol.* 47, 145-147 (1978)) both indicated that hPS12 is largely hydrophilic except for the N-terminal amino acids. The N-terminal 34-35 amino acids have the characteristics of a putative signal peptide as observed for hPS11. The N-terminal domain of hPS12, as in hPS2, is hydrophobic.

Comparison of the domain structure of hPS12, hPS11 and hPS2 shows that hPS12 is very similar to hPS11. There is 90.6% homology at the amino acid level and 93.7% homology at nucleotide level between hPS12 and hPS11. The cysteine residues and majority of the glycosylation sites are conserved. Both hPS12 and hPS11 differ from hPS2 by having an extra n-subdomain and but not a hydrophobic c-terminal domain. Examples 1-3 demonstrate that there are multiple species of highly homologous SP1-like proteins present in the human placenta, including at least one membrane bound and one cytoplasmic or secretory protein.

EXAMPLE 4

Isolation and Characterization of cDNA Encoding SP1-like Proteins Expressed in Cells of Testis and Placental Origin The presence of SP1 in human testis was shown by Western blot analysis of testicular homogenate with anti-placental SP1 antibodies. Instead of two major hybridization bands corresponding to 72 kDa and 61.5 kDa, as observed with human placental extract, testicular homogenate shows only one weakly hybridizing band corresponding to 47 kDa. The presence of SP1 in testis was further confirmed by Northern blot analysis with labelled placental SP1 CNA as the probe. Screening of human testis cDNA library with placental SP1 cDNA as the probe yielded 17 positive clones which can be divided into four groups according to their restriction enzyme maps.

The procedure was as follows. A partial cDNA clone of SP1, lambda hPS3, was isolated from a human placental library. The nucleotide sequence is shown in FIG. 5. Lambda hPS3 cDNA includes the 5' nontranslating sequence and the N-terminal 48 amino acids of human SP1. This cDNA insert subcloned into M13mp18 was released from the recombinant phage with EcoRI, fractionated by electrophoresis in 3.5% polyacrylamide gel, and recovered by electroelution according to the method of T. Maniatis et al., *Molecular Cloning: A Laboratory Manual* pp. 167, 173-177, 184 (Cold Spring Harbor Laboratory, Cold Spring Harbor, N.Y. 1982). SP1 cDNA was labeled by nick translation with DNase 1 and DNA polymerase 1 in the presence of 15 $\mu$Ci of each of the ($\alpha$-$^{32}$P) deoxynucleotides according to the methods of M. W. Rixon et al., *Biochemistry* 22, 3237-3244 (1983). The nick translated probe was desalted through an AcA 54 column and denatured before use.

Group 1, contains two clones, lambda hTS2 and lambda hTS3. Estimation of cDNA insert size by polyacrylamide gel electrophoresis and nucleotide sequence analysis shows that both clones are about 550 bp, and are identical to nucleotide base 433 to 910 of placental SP1 cDNA hPS11, shown in FIG. 2. These clones do not have internal EcoRI sites.

Group 2 consists of three clones, hTS1, hTS7 and hTS13. cDNA inserts of this group have an internal EcoRI site. Sequence analysis of the 3' 750 bp EcoRI fragment of the longest cDNA, hTS1, shows that it has 95.9% homology with nucleotide base 1332 to 1930 of hPS11. The nucelotide sequence of 3' EcoRI fragment of hTS1, termed hTS1L, as compared with the nucelotide sequence of hPS11, is shown in FIG. 6. The 5' EcoRI fragment appears to indicate that the group 1 and group 2 clones are allelic gene products.

Group 3 consists of three clones, hTS5, hTS6, and hTS9. Sequence analysis of these clones shows that they are identical to pSP1-i, one of the placental SP1 cDNA reported by Rooney, et al., *Gene* 71, 439-449 (1988).

Group 4 consists of nine clones. Five cDNAs of this group were sequenced. Their nucleotide sequences are identical. The nucleotide sequence of the longest clone, hTS16, is shown in FIG. 7, along with the potential glycosylation sites, conserved cysteine residues, and the boundaries of the exon/intron and domain regions. It has 1957 bp and is apparently an incompletely spliced product of the SP1 gene. The sequences marked as IVS1 and IVS2 have no homology with any SP1 cDNA sequence known and are apparently unspliced introns. There is also a deletion of 161 bp within the coding sequence (between nucleotide bases 1314 and 1315). The presumed introns and the deletion of hTS16 occur between boundaries of the different domains. This is similar to what was observed regarding the positions of introns in a different SP1 gene by Oikawa, et al., *Biochem. Biophys. Res. Comm.* 156, 68-77 (1988). The segments of sequence marked N, R1n, R2n, R2c and C and the sequence after the stop codon are identical with that of the group 3 clones and encode a protein identical to pSP1-i.

EXAMPLE 5

Isolation and Characterization of cDNA Encoding SP1-Like Proteins Expressed in HeLa Cells and Hematopoietic Cells Screening of a HeLa cell library using hPS3 probe yields 10 positive clones with cDNA inserts varying from 630 to 950 bp in size, as indicated by polyacrylamide gel electrophoresis. Southern blot analysis shows that the HeLa cell clones are highly homologous to placental SP1 cDNA. The nucleotide sequence of one of the HeLa cell cDNA clones, hHS2, was determined.

FIG. 8 shows the nucleotide sequence and the encoded amino acids of hHS2. hHS2 has 756 bp with an open reading frame encoding 248 amino acids. Alignments of hPS11 and hHS2 according to the different domains at the nucleotide level and at the protein level demonstrate that hHS2 cDNA contains the N-terminal domain, the first internal repeat and part of the second repeat of hPS11. Percent homology with the corresponding domains in hPS11 is 92.5, 95.0 and 92.7, respectively, at the nucleotide level, and 87.1, 88.2 and 94 at the amino acid level. The positions of the cysteine residues and the potential glycosylation site are conserved in hPS11 and hHS2.

SP1 mRNA has also been identified in different hematopoietic cells. Expression of different SP1 genes appears to be lineage specific. Culture cells were stimulated for four hours with 10 ng/ml of phorbol 12-myristate 13-acetate (PMA) (P), 5 μg/ml lipopolysaccharide (LPS) (L), 100U/ml interferon-gamma (INF-gamma) (gamma), or the combination of LPS and IFN-gamma (L.gamma). Northern blot analysis revealed the presence of hybridizing mRNA in unstimulated cells (C) with a 2.4 kb band in the KG-1 line (myelomonocytic) and a 3.3 kb band in the HEL line (erythroid). Stimulation with LPS and IFN-gamma have little effect on SP1 mRNA expression in KG-1 over a four hour period. However, LPS plus IFN-gamma increases SP1 mRNA expression in HEL several fold. The results demonstrate for the first time both expression of the SP1 genes in hematopoietic cells and differential expression of the SP1 genes.

EXAMPLE 6

Isolation and Characterization of cDNA Encoding SP1-Like Proteins Expressed in Cells of Intestinal Origin A human intestine cDNA library was screened with hPS3 using procedures described in Example 5. 21 positive clones were identified. Analysis with restriction enzymes showed that these clones can be divided into four main groups. Four of the clones have one internal EcoRI site. Polyacrylamide gel electrophoresis analysis showed that the longest clone of this group, hIS1, gave two insert fragments of 1.1 kb and 1.3 kb upon digestion with EcoRI. 17 cones have no internal EcoRI sites but include an interna XbaI site. The longest clone in this group is hIS3 with a cDNA insert of 1.5 kb. The other three groups do not have internal XbaI sites and have similar restriction enzyme maps as those of the three groups of placental SP1 cDNA. The smaller EcoRI fragments of clones hIS1and hIS2 of the first group have been sequenced. cDNA inserts of these two clones are identical.

FIG. 9 shows the nucleotide sequence and the encoded amino acids of hIS1. hIS1has 1024 bp with a 5' non-translated sequence of 61 bp, an open reading frame of 963 bp encoding a potential signal peptide of 34 amino acids, an N-terminal domain of 107 amino acids and a complete repeating unit consisting of an n-subdomain of 93 amino acids and a c-subdomain of 85 amino acids. Comparison of the corresponding domains of hIS1 and hPS11 shows that the percentage of homology between the two cDNAs is approximately 74.5, with the highest homology between the n-subdomains (79.3%) and the lowest homology between the c-subdomains (68.3%). The percentage homology of the encoded amino acid sequence of the two cDNAs is approximately 57.4, and is also higher between the n-subdomains and lower between the c-subdomains.

EXAMPLE 7

Comparison of Members of the Pregnancy-Specific β1 Glycoprotein (SP1)

A human genomic library was screened, clones identified and restriction mapped, as described in Examples 1-3. Partial restriction maps were constructed which demonstrated the presence of at least seven groups of unique SP1 genomic clones and suggested that multiple genes code for SP1. The multigene nature of SP1 was confirmed by hybridization of the SP1 cDNA probe to multiple bands on Southern blots of human genomic DNA. Further analysis with chromosomal DNA dot blot demonstrated the presence of homologous sequences on the X chromosome and autosomal chromosome 6.

The methods and materials used to localize the SP1 genes using a mixture of labeled hPS2 and hPS3 cDNAs to screen a human genomic library was reported by Chan, et al., in *Am. J. Hum. Genet.* 43,152–159 (1988).

Comparison of the encoded amino acid sequence of all SP1 cDNAs was used to derive a consensus sequence, shown in FIG. 11. During derivation of the consensus sequence for the amino coding region hPS11, PSG16, PSBGC and PSBGD were considered as one unit because of their near identical coding sequence and the probability that they are products of the same gene. An amino acid or nucleotide is considered to be consensus if it occurs at least three times among the clones hPS12, hPS2, PSBGE, pSP1-i and hPS11/PSG16/PSBGC-D. All cDNAs showed a high degree of homology in the regions compared. Percent of homology with the consensus amino acid sequence ranged from 92.5 to 100% in the N-terminal domain and the n-subdomains except for the N-terminal domain of hPS2 which shows only 85.9% homology. Levels of homology among the c-subdomains are slightly lower than the other domains and range from 85.9 to 97.6%. Nucleotide sequence homology of the N-terminal and n- and c-subdomains are similar to that of amino acid sequences and range from 90 to 99%. In contrast, the amino acid and nucleotide sequences of the C-terminal domain of these cDNAs share very little sequence homology with two exceptions: the C-terminal domain of hPS11 and PSBGD are identical and the 3' non-coding sequence of PSG16 is identical with that of hPS11 other than for the deletion of 86 bp near the 3' end of the coding region. Positions of the cysteine residues in the n- and c- subdomains of all cDNAs are conserved. Positions of the potential glycosylation sites in the N-terminal domain and R1n-subdomain are also conserved.

Comparison of the aligned amino acid sequences encoded by human placental SP1 cDNAs shows that hPS12 differs from the other SP1 cDNAs in the deletion of three nucleotides encoding Ile-90 in the N-terminal domain. The comparison also makes clear that hPS12 and pSP1-i are different from each other as well as the other SP1 cDNAs. Again, hPS11 and PSBGD are identical. PSG16 is identical to hPS11 except at four positions in the coding region resulting in the change of three amino acids, a G to C mutation in the 3' non-coding sequence and deletion of 86 bp near the 3' end of the coding region. PSBG is also identical to hPS11 and PSBGD except for the C-terminal domain.

Both hPS2 and PSBGE have one less n-subdomain when compared to the other SP1 cDNAs. The n-subdomain of hPS2 and PSBGE are more comparable with the R1n-subdomain than the R2n-subdomain. The percentage of homology with the R1n-subdomain consensus sequence is 93.5 and 92.5 and that of the R2n-subdomain is 52.7 and 48.4 for hPS2 and PSBGE respectively. The c-subdomain of hPS2 and PSBGE are less homologous to the consensus sequence than that of the other SP1 cDNAs, being 87.1% and 85.9% respectively, while all other cDNAs show greater than 90% homology. The most significant difference between hPS2 and the other SP1s is the presence of the 81 amino acid hydrophobic C-terminus while all other SP1s have only relatively short (14 amino acids or less) hydrophilic C-termini.

Comparison of the 5' non-coding sequence of several SP1 cDNAs shows over 91% similarity among all of the SP1 sequences. Comparison of the 3' non-coding sequences produces more variation. The 3' non-coding sequence of hPS2 has very little homology with any of the SP1 cDNAs reported. On the other hand, the 3' non-coding sequence of hPS12 is very homologous to that of PSBGE and pSP1-i. Aside from 27 bp, 30 bp and 39 bp at the 5' end of this region in hPS12, PSBGE and pSP1-i, respectively, there is 95% homology among the three cDNAs. The 3' non-coding sequences of hPS11, PSG16 and PSBGD are almost identical except for the deletion of 70 bp after the stop codon in PSG16 and one mismatch in both PSG16 and PSBGD when compared with hPS11.

All the SP1 cDNAs reported demonstrate characteristics required for inclusion in the Ig gene superfamily, namely sequence homology, characteristic domain structure, conserved disulfide bond, within domains and beta sheet structure.

The evidence shown in Examples 1 to 6 suggests the presence of multiple species of highly homologous SP1 proteins in human placenta and that the SP1 proteins are encoded by multiple genes.

The results shown in Examples 1 to 3 support the contention that SP1 protein in human placenta consists of products of three or more genes. Two of the reported placental SP1 cDNAs, hPS11 and PSBGD are identical. PSG16 and another partially sequenced cDNA PSG93 differ from these two cDNAs at only four bases which could correspond to polymorphisms. Based on their almost identical protein coding sequences, hPS11, PSG16, PSBG93, PSBGC and PSBGD, are likely to be the products of the same gene with differentially spliced exons encoding the C-terminus and 3' non-coding sequence. Three other cDNAs hPS12, PSBGE and pSP1-i have 221 bp in their 3' non-coding sequence which are highly homologous (95%). Considering that this is observed in the non-coding region and that the three clones are derived from two different libraries, it is conceivable that the few differences are individual polymorphisms. These three cDNAs are products of splicing of different amino acid coding exons to one common exon which contains the 3' non-coding sequence. The exon encoding the N-terminal domain of hPS12 is unique in that it has a 3 bp deletion when compared to the other cDNAs. PSBGE differs from hPS12 and pSP1-i by having one less n-subdomain which could be the result of difference in splicing. The gene encoding hPS12/PSBGE/pSP1-i could be different from that encoding hPS11/PSG16/PSG93/PSBGC-D. The other SP1 cDNA, hPS2, is unique. It has no significant homology with any of the SP1 cDNAs reported.

The presence of three different species of mRNA in human placenta was confirmed by the Northern blot analysis. The 3' EcoRI fragment of hPS11 contains the entire 3' non-coding sequence and is specific for that cDNA. The NcoI-EcoRI fragment of hPS12 contains the C-terminal 24 bp of the coding sequence and the 3' non-coding sequence and is unique for cDNAs of this group. The probe for hPS2 is the fragment encoding the unique hydrophobic C-terminal domain of the molecule. These three probes are cDNA specific. Hybridization of the Northern blot with these probes therefore indicates the presence of the specific mRNA species. The hPS2 specific probe hybridized to both the 1.65 Kb and 2.25 Kb mRNA bands, suggesting that each mRNA band contains more than one species of mRNA. Up to the present time only one placental SP1 cDNA with sequence encoding a hydrophobic C-terminal has been found. The Northern blot results suggest that there may be more than one species of membrane-bound SP1 present in human placenta.

Multiple mRNAs have also been reported for the CEA gene family. The SP1 genes, like the CEA family of genes, are probably localized in clusters on chromosome 6 and the X chromosome, although there is also the possibility that all SP1 cDNAs so far reported are derived from one very large gene which gives rise to the above three groups of products by differential splicing.

Both hPS2 and PSBGE, unlike the other SP1 cDNAs, contains only one n-subdomain. These cDNAs could be formed by having one complete repeating unit containing an n-subdomain and c-subdomain (i.e. n-subdomain in hPS2 is R2n-subdomain) or by splicing the n-subdomain of one repeating unit with the c-subdomain of another repeating unit (i.e. n-subdomain in hPS2 is R1n-subdomain). By comparisons with the consensus sequence of R1n- and R2n-subdomains of the SP1 cDNAs, it is that the n-subdomain of hPS2 is likely to be derived from the R1 repeating unit instead of the R2 repeating unit. A similar conclusion is drawn for PSBGE.

The distinctive feature of hPS2, the presence of an 81 amino acids hydrophobic C-terminus, is very similar to that observed in CEA, TM-CEA and NCA. Hydropathy plot analysis showed that this C-terminal domain of hPS2 is very hydrophobic and supports the inference that it represents the membrane-anchor region of the molecule. These results support the theory that there are two types of SP1 proteins in human placenta, the cytoplasmic or soluble SP1 and the membrane-bound SP1. Analogous phenomenon has been reported for the CEA family of proteins.

Even though the SP1 proteins and CEAs appear to share a lot of common properties, there are sufficient features unique to the SP1 proteins to qualify them as a separate subfamily of the Ig gene superfamily instead of being members of the CEA gene subfamily. For example, even though the SP1s are very similar to CEA and NCA, the homology among the different SP1 family members are even higher, being consistently greater than 90% at the nucleotide level and greater than 85% at the amino acid level. The SP1 proteins are : also less glycosylated. The number of potential glycosylation site ranges from four in pSP1-i to eight in PSBGC with the majority having six or seven. Most of these sites are also conserved. Both CEA and NCA are more, heavily glycosylated, with twenty-seven potential sites in NCA and twelve potential sites in NCA. A number of these sites are conserved between CEA and NCA but not between CEAs and SP1s.

The strong conservation of both nucleotides and amino acids among the internal repeats of SP1 and CEA genes suggests that both gene families evolved recently by the duplication of a primordial gene. The percentage homology at the amino acid level between the R1n-subdomain and R2n-subdomain of SP1 is 52.7, which is significantly lower than that between the R1n-subdomain of SP1 and the n-subdomains of CEA (62.4 with IA, 57.0 with IIA, and 59.1 with IIIA) and the n-subdomains of NCA (62.4). It is comparable with the percentage similarity between the R2n-subdomain and the n-subdomains of CEA and NCA. Comparison of nucleotide homology gives the same results, suggesting that the duplication of R1 repeat unit to R2 repeat unit occurred before the divergence of SP1 and CEA and that the divergence of the two genes involved the duplication of the R1 repeat unit only.

EXAMPLE 8

Comparison of CEA and SP1 Proteins and Removal of Cross-Reactive Proteins from CEA Assays As described above, cDNA clones for seven apparently different, but closely related, genes for SP1 proteins have been isolated. One group of clones appears to encode placenta-specific SP1 proteins. Clones in this group are characterized by not having an internal EcoRI site. An example is hPS12. A second group of clones, reported by Chan, et al., *DNA* 7(8), 545–555 (1988), includes hPS11, which has one internal EcoRI site, and has been isolated from placenta and non-placental sources, including testis, although it is not known whether hPS11 is secreted from normal testis into the blood stream. While similar, hPS11 differs from the βSG16 reported by Watanabe and Chou, *J. Biol. Chem.* 263(4), 2049–2054 (1988), at amino acids 41, 43 and 319, and 86 nucleotides near the 3' end of the coding regions. A third group of clones has been isolated only from placenta and has two internal EcoRI sites. An example of the third group is hPS2.

Figure 10:
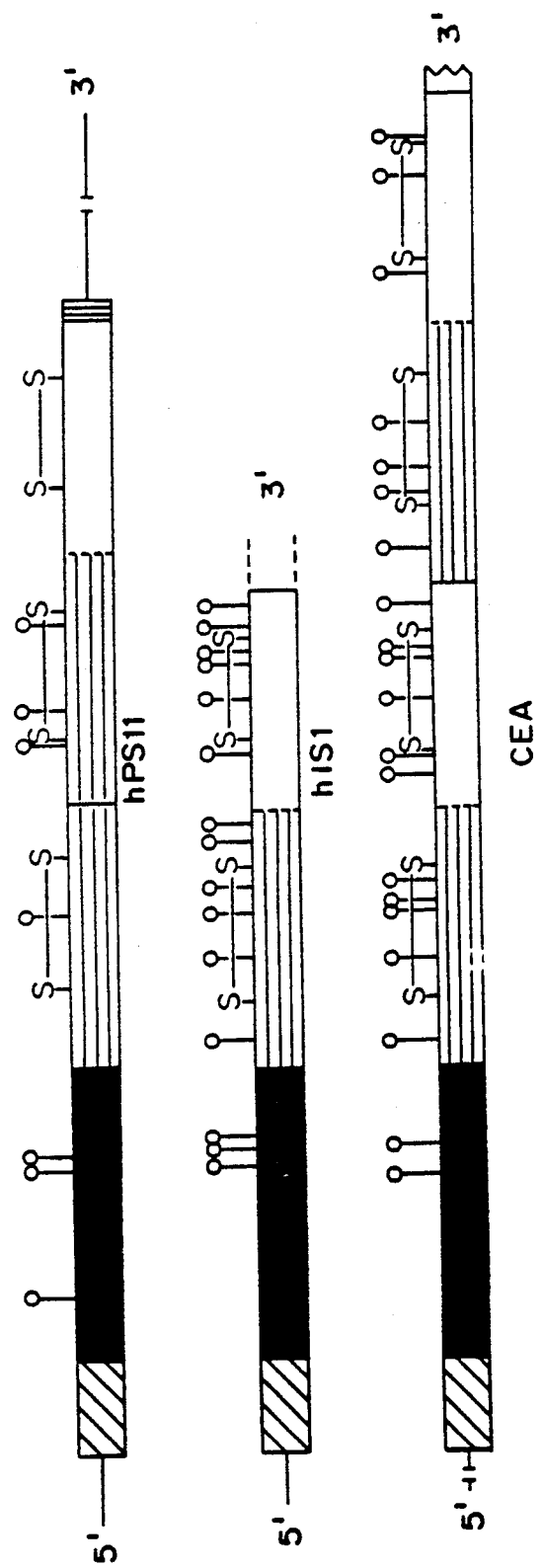
FIG. 10 is a comparison of the domain structure of hPS11, hIS1 and CEA. The following legend is used.

Clones have also been isolated from a HeLa cell cDNA library, a testis cDNA library and an intestinal cDNA library, which are highly homologous to placental SP1 cDNA.

hIS1 shows higher homology to Normal Crossreacting Antigen (NCA), a member of the CEA family, than to the placental sP1 cDNAs. FIG. 10 compares the domain structures among hPS11, hIS1 and CEA. hIS1 is 93% homologous at the nucleotide level, and 67% homologous at the amino acid level, with CEA. The N-terminal domains of both hIS1 and CEA are two amino acids shorter than that of hPS11. The domain structure, as well as the number of potential glycosylation sites, are more similar between hIS1 and CEA than hPS11.

All cloned SP1 cDNAs show significant structural homology with carcinoembryonic antigen (CEA). CEA is a large membrane glycoprotein present in high quantities in adenocarcinomas of endodermally derived digestive tract epithelia and fetal colon. There are a number of molecules closely related immunologically to CEA. These molecules have very similar but distinct amino-terminal amino acid sequences and have been postulated to be encoded by. different genes by Shively and Beatty (1985). As shown in the foregoing examples, the SP1 genes encode proteins which are structurally and chemically similar to CEA and are expressed, at least in part, in tissue where CEA is also expressed. Among the placental SP1 cDNAs, hPS2 and PSBGE have the domain structure closest to that of CEA and NCA. Both hPS2 and PSBGE, similar to NCA, have only one complete repeat unit, i.e, one n-subdomain and one c-subdomain, while CEA has three complete repeating units. All other SP1 cDNAs have one complete repeating unit and an additional n-subdomain. Comparison of the consensus amino acid sequences of the different domains of the SP1 cDNAs with the corresponding domains in CEA and NCA shows that the percentage homology of both CEA and NCA to SP1 is quite similar in all domains compared, ranging from 53.8% to 62.4% at the amino acid level. Nucleotide sequence comparison of the different domains of SP1, CEA and NCA showed similar results as that of amino acid comparison.

It is therefore possible to use the nucleotide and protein sequences for the SP1-like proteins to screen reagents used in detecting CEA, to thereby decrease the number of false positives arising due to detection of the SP1-like proteins rather than the CEA, in various clinical circumstances including but not limited to monitoring and detection of tumors of the gastrointestinal tract.

EXAMPLE 9

Use of Purified SP1 Protein as an Immunosuppressive Agent

Immunological studies show that pure human placental SP1 (containing all species of SP1 protein present in the placenta capable of reacting with the same antibodies) at a concentration of as low as 10 μg/ml inhibits lymphocyte proliferation significantly (50%) in a mixed lymphocyte assay. Inhibition is 85% at 30 μg/ml and 100% at 100 μg/ml. The results of two independent studies are shown in FIG. 12. This immunosuppressive effect of SP1 appears to be specific since phytohemagglutinin (PHA) stimulated lymphocytes are not affected by comparable dosage of SP1. The results confirm the structural evidence for an immunological role for the placental SP1 proteins.

EXAMPLE 10

Use of Purified SP1 Protein as a Growth Factor

Growth promoting activity of placental SP1 was tested by addition of varying amounts of pure human placental SP1 preparation to serumless murine bone marrow cultures. The effect of SP1 was followed by assessing the number and size of hematopoietic precursor cells such as megakaryocytes as well as measuring acetylcholinesterase (AchE) activities. Addition of SP1 to murine bone marrow cultures induced a significant increase in the diameter of megakaryocytes. The potency of SP1 in inducing megakaryocytopoiesis is comparable to that of interleukin 6, an established growth factor stimulator for megakaryocytes. The effect of SP1 on murine megakaryocyte AchE is shown in FIG. 13. SP1 at a concentration of as low as 10 ng/ml caused a 45% increase in AchE activity of megakaryocytes. These results demonstrate that SP1 has growth promoting activities.

EXAMPLE 11

Use of Pregnancy-Specific Proteins and Nucleic Acid Sequences as Pharmaceutical Agents There are at least three proteins, including the protein encoded by hPS11, hPS2 and hPS12, which appear to be expressed in placental tissue. hPS2 and hPS12 have only been found in placental tissue. Since placental tissue exists only in individuals who are pregnant, the levels of hPS11, hPS2 and hPS12 proteins can function as an index of whether the female, either a human or non-human mammal such as a rat, cow or pig, is pregnant. The present invention therefore includes a method and reagents for testing for pregnancy wherein a biological sample from the subject is assayed for the level of one of the placenta specific peptides, and correlating an above-normal level, if any, with pregnancy, and correlating a normal or below-normal level, if any, with the absence or abnormalities of pregnancy.

In one embodiment of the pregnancy testing method of the present invention, a biological sample from the female is obtained and is treated with monoclonal antibodies against the protein described in FIG. 2. The level of antibody-protein reaction is measured using methods known to those skilled in the art (i.e., radiolabelling, ELISA, etc.) to determine the level of protein in the sample.

The present invention also includes a method and compositions for enhancing the fertility of a female deficient in one of the placenta specific proteins such as the protein described in FIG. wherein an effective amount of the protein or peptide is administered to the female.

The peptide is preferably administered in combination with a pharmaceutically acceptable carrier, as described below. The preferred dosage of the peptide is based on the normal levels of the protein and is preferably administered as determined by those skilled in the art. In general, this will be between 0.1 and 50 mg/kg body weight. Any pharmaceutically acceptable carrier may be selected which will maintain the biological activity of the protein, such as 5% dextrose in sterile water and sterile normal saline.

The present invention further includes a method and compositions for enhancing the viability of a fetus wherein an effective amount of a pregnancy specific peptide or protein such as the one shown in FIG. 2 is administered to either the mother or the fetus. If the mother has an inadequate level of SP1-like proteins, a spontaneous abortion could occur. Accordingly, the administration of the composition can raise the level of SP1 proteins necessary to maintain a viable fetus. The peptide is preferably administered in combination with a pharmaceutically acceptable carrier, as described above.

The SP1 proteins described here are present in cows, pigs, sheep, horses, dogs, cats, rats, and primates, including chimpanzee, cynomolgus, monkeys, and baboons, as well as humans. On this basis, it is assumed that the proteins are present in all placental mammals, and that the methods described above can therefore be utilized in all placental mammals.

Modifications and variations of the present invention, proteins expressed from nucleotide sequences encoding members of the SP1 protein family, antibodies and hybridization probes to the proteins and sequences, and methods for use thereof, will be obvious to those skilled in the art from the foregoing detailed description of the invention. Such modifications and variations are intended to come within the scope of the appended claims.

We claim:

1. A method for stimulating growth and proliferation of hematopoietic cells comprising:
   administering an effective amount of a purified pregnancy-specific $\beta$-1 glycoprotein to the cells to stimulate growth and proliferation of the hematopoietic cells.

2. The method of claim 1 wherein the protein is of placental origin.

3. The method of claim 2 wherein the protein is isolated by binding to antibodies to SP1 proteins.

* * * * *